US006531314B1

(12) United States Patent
Arena et al.

(10) Patent No.: US 6,531,314 B1
(45) Date of Patent: Mar. 11, 2003

(54) GROWTH HORMONE SECRETAGOGUE RECEPTOR FAMILY

(75) Inventors: Joseph P. Arena, Eagleville, PA (US); Doris F. Cully, Scotch Plains, NJ (US); Scott D. Feighner, Highlands, NJ (US); Andrew D. Howard, Park Ridge, NJ (US); Paul A. Liberator, Holmdel, NJ (US); James M. Schaeffer, Westfield, NJ (US); Leonardus H. T. Van Der Ploeg, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/077,674

(22) PCT Filed: Dec. 10, 1996

(86) PCT No.: PCT/US96/19445

§ 371 (c)(1),
(2), (4) Date: Jun. 3, 1998

(87) PCT Pub. No.: WO97/21730

PCT Pub. Date: Jun. 19, 1997

(51) Int. Cl.$^7$ ............................................. C12N 15/00

(52) U.S. Cl. ...................... 435/325; 536/23.1; 536/23.5; 530/350; 435/69.1; 435/320.1

(58) Field of Search ........................ 530/350; 536/23.5, 536/23.1; 435/320.1, 325, 69.1

(56) References Cited

U.S. PATENT DOCUMENTS

| | | | | |
|---|---|---|---|---|
| 3,239,345 | A | 3/1966 | Hodge et al. ................... 99/2 |
| 4,036,979 | A | 7/1977 | Asato ......................... 424/275 |
| 4,410,513 | A | 10/1983 | Momany ..................... 424/177 |
| 4,411,890 | A | 10/1983 | Momany ..................... 424/177 |
| 5,057,417 | A | 10/1991 | Hammonds ................. 435/69.1 |
| 5,206,235 | A | 4/1993 | Fisher et al. ................. 514/213 |
| 5,245,011 | A | * 9/1993 | Tiberi ......................... 530/350 |
| 5,283,241 | A | 2/1994 | Bochis et al. ............... 514/183 |
| 5,284,841 | A | 2/1994 | Chu et al. ................... 514/183 |
| 5,310,737 | A | 5/1994 | Fisher et al. ................. 514/215 |
| 5,317,017 | A | 5/1994 | Ok et al. .................... 514/211 |
| 5,374,721 | A | 12/1994 | Schoen et al. .............. 540/491 |
| 5,422,265 | A | * 6/1995 | Civelli ....................... 435/252.3 |
| 5,430,144 | A | 7/1995 | Schoen et al. .............. 540/461 |
| 5,434,261 | A | 7/1995 | Schoen et al. .............. 540/461 |
| 5,438,136 | A | 8/1995 | Devita et al. .............. 5640/456 |
| 5,492,916 | A | 2/1996 | Morriello et al. ........... 514/318 |
| 5,494,919 | A | 2/1996 | Morriello et al. ........... 514/323 |
| 5,494,920 | A | 2/1996 | Chen et al. ................. 514/323 |
| 5,583,010 | A | 12/1996 | Baumbach et al. ......... 435/69.1 |
| 5,591,641 | A | 1/1997 | Thorner et al. ............. 435/69.1 |

FOREIGN PATENT DOCUMENTS

| | | |
|---|---|---|
| EP | 0144230 | 12/1984 |
| EP | 0513974 | 3/1992 |
| WO | WO 89/07110 | 8/1989 |
| WO | WO 89/07111 | 8/1989 |
| WO | WO 89/04081 | 3/1993 |
| WO | WO 94/07486 | 4/1994 |
| WO | WO 94/08583 | 4/1994 |
| WO | WO 94/11012 | 5/1994 |
| WO | WO 94/13696 | 6/1994 |
| WO | WO 94/19367 | 9/1994 |
| WO | WO 95/03289 | 2/1995 |
| WO | WO 95/03290 | 2/1995 |
| WO | WO 95/09633 | 4/1995 |
| WO | WO 95/11029 | 4/1995 |
| WO | WO 95/12598 | 5/1995 |
| WO | WO 95/13069 | 5/1995 |
| WO | WO 95/14666 | 6/1995 |
| WO | WO 95/16675 | 6/1995 |
| WO | WO 95/16692 | 6/1995 |
| WO | WO 95/17422 | 6/1995 |
| WO | WO 95/17423 | 6/1995 |
| WO | WO 95/34311 | 12/1995 |
| WO | WO 96/02530 | 2/1996 |

OTHER PUBLICATIONS

Grenader, American Journal of Physiology, vol.268/No. 3/Part 2, pp. F423–F434, Mar. 1995.*

Julius et al., Science 241:558–564, Jul. 29, 1988.*

Williams, Textbook of Endocrinology, p. 790, 1994.*

Ok, et al., "Structure–Activity Relationships of the Non–peptidyl Growth Hormond Secretagogue L–692, 429", Bioorg. & Med. Chem. Letters, vol. 4, No. 22, pp. 2709–2719 1994.

Patchett, et al., "Design and biological activities of L–163, 191 (MK–0677): A potent, orally active growth hormond secretagogue", Proc. Natl. Acad. Sci. USA, vol. 92, pp. 7001–7005, Jul. 1995.

Schoen, et al., "Section IV: Immunology, Endocrinology and Metaboles", Ann. Rep. in Med. Chem., vol. 28, pp. 177–183 (1993).

Chem., vol. 28, pp. 177–183 (1993).

Smith, et al., "A Nonpeptidyl Growth Hormone Secretagogue", Science, vol. 260, pp. 1640–1643, Jun. 11, 1993.

Aloi, et al., J. of Clin. End. and Met., vol. 79, No. 4, pp. 943–949, 1994.

(List continued on next page.)

Primary Examiner—Lorraine Spector
Assistant Examiner—Eliane Lazar-Wesley
(74) Attorney, Agent, or Firm—Jack L. Tribble; Anna L. Cocuzzo

(57) ABSTRACT

Human, swine and rat growth hormone secretagogue receptors have been isolated, cloned and sequenced. Growth hormone secretagogue receptors are new members of the G-protein family of receptors. The growth hormone secretagogue receptors may be used to screen and identify compounds which bind to the growth hormone secretagogue receptor. Such compounds may be used in the treatment of conditions which occur when there is a shortage of growth hormone, such as observed in growth hormone deficient children, elderly patients with musculoskeletal impairment and recovering from hip fracture and osteoporosis.

24 Claims, 31 Drawing Sheets

OTHER PUBLICATIONS

Bowers, et al., J. of Clin. End. and Met., vol. 79, No. 4, pp. 940–942, 1994.

Sethumadhavan, et al., "Demonstration and Characterization of the Specific Binding of Growth Hormone–Releasing . . . ", Biochem., Biophys. Res. Comm., vol. 178, pp. 31–37, 1991.

Howard, et al., "A Receptor in Pituitary and Hypothalamus That Functions in Growth Hormone Release", Science, vol. 273, pp. 974–977, 1996.

King, et al., Science, vol. 250, pp. 121–123, 1990.

Julius, et al., Science, vol. 241, pp. 558–564, 1988.

Cubitt, et al., Trends Biochem. Sci., vol. 20, pp. 448–455, 1995.

McKee, et al., "Molecular analysis of pituitary and hypothalmic growth hormone secretagogue receptors", Molecular Endocrinology, vol. 11, pp. 415–423, 1997.

Feighner, et al., "Structural Requirements For the Activation of the Human Growth Hormone Secretagogue Receptor (GHS–R) . . . ", Molecular Endocrinology, vol. 12, pp. 137–145, 1997.

* cited by examiner

```
          10        20        30        40
           .         .         .         .
     CCTCACGCTGCCAGACCTGGGCTGGGACGCTCCCCCTGAA   40
     AACGACTCGCTAGTGGAGGAGCTGCTGCCGCTCTTCCCCA   80
     CGCCGCTGTTGGCGGGCGTCACCGCCACCTGCGTGGCGCT  120
     CTTCGTGGTGGGTATCGCGGGCAACCTGCTCACGATGCTG  160
     GTAGTGTCACGCTTCCGCGAGATGCGCACCACCACCAACC  200

210       220       230       240
           .         .         .         .
     TCTACCTGTCCAGCATGGCCTTCTCCGACCTACTCATCTT  240
     CCTCTGCATGCCCCTCGACCTCTTCCGCCTCTGGCAGTAC  280
     CGGCCTTGGAACCTTGGCAACCTGCTCTGCAAACTCTTCC  320
     AGTTCGTTAGCGAGAGCTGCACCTACGCCACAGTGCTCAC  360
     CATCACCGCGCTGAGCGTCGAGCGCTACTTCGCCATCTGC  400

410       420       430       440
           .         .         .         .
     TTCCCGCTGCGGGCCAAGGTAGTGGTCACCAAGGGCCGGG  440
     TAAAGCTGGTCATCCTGGTCATCTGGGCCGTGGCCTTCTG  480
     CAGCGCCGGGCCCATCTTCGTGCTGGTCGGAGTGGAGCAT  520
     GATAACGGCACTGACCCTCGGGACACCAACGAGTGCCGCG  560
     CCACGGAGTTCGCCGTGCGCTCCGGGCTGCTTACCGTCAT  600

610       620       630       640
           .         .         .         .
     GGTCTGGGTGTCCAGTGTCTTCTTCTTCCTGCCTGTCTTC  640
     TGCCTCACTGTGCTCTATAGCCTCATCGGCAGGAAGCTCT  680
     GGCGGAGGAAGCGCGGCGAGGCGGCGGTGGGCTCCTCGCT  720
     CAGGGACCAGAACCACAAACAAACCGTGAAAATGCTGGCT  760
     GTAGTGGTGTTTGCTTTCATACTCTGCTGGCTGCCTTTCC  800

810       820       830       840
           .         .         .         .
     ATGTAGGGCGATATTTATTTTCCAAATCCTTGGAGCCTGG  840
     CTCTGTGGAGATTGCTCAGATCAGCCAATACTGCAACCTC  880
     GTGTCCTTTGTCCTCTTCTACCTCAGTGCGGCCATCAACC  920
     CTATTCTGTACAACATCATGTCCAAGAAGTATCGGGTGGC  960
     GGTGTTCAAACTGCTGGGATTTGAGCCCTTCTCACAGAGG 1000

1010      1020      1030      1040
           .         .         .         .
     AAACTCTCCACTCTGAAGGATGAAAGTTCTCGGGCCTGGA 1040
     CAGAATCTAGTATTAATACATGA 1063 (SEQ ID NO:1)
```

FIG. 1

```
           10          20
           .           .
    MLVVSRFREM  RTTTNLYLSS   20
    MAFSDLLIFL  CMPLDLFRLW   40
    QYRPWNLGNL  LCKLFQFVSE   60
    SCTYATVLTI  TALSVERYFA   80
    ICFPLRAKVV  VTKGRVKLVI  100

110         120
           .           .
    LVIWAVAFCS  AGPIFVLVGV  120
    EHDNGTDPRD  TNECRATEFA  140
    VRSGLLTVMV  WVSSVFFFLP  160
    VFCLTVLYSL  IGRKLWRRKR  180
    GEAAVGSSLR  DQNHKQTVKM  200

210         220
           .           .
    LAVVVFAFIL  CWLPFHVGRY  220
    LFSKSLEPGS  VEIAQISQYC  240
    NLVSFVLFYL  SAAINPILYN  260
    IMSKKYRVAV  FKLLGFEPFS  280
    QRKLSTLKDE  SSRAWTESSI  300

310         320
           .           .
       NT 302 (SEQ ID NO:2)
```

FIG. 2

```
1                                    30
LTLPDLGWDA  PPENDSLVEE  LLPLFPTPLL

HELIX 1                              60
AGVTATCVAL  FVVGIAGNLL  TMLVVSRFRE

HELIX 2     90
MRTTTNLYLS  SMAFSDLLIF  ICMPLDLFRL

HELIX 3  120
WQYRPWNLGN  LLCKLFQFVS  ESCTYATVLT

150
ITALSVERYF  AICFPLRAKV  VVTKGRVKLV

HELIX 4                      180
ILVIWAVAFC  SAGPIFVLVG  VEHDNGTDPR

210
DTNECRATEF  AVRSGLLTVM  VWVSSVFFFL

HELIX 5                          240
PVFCLTVLYS  LIGRKLWRRK  RGEAAVGSSL

HELIX 6              270
RDQNHKQTVK  MLAVVVFAFI  LCWLPFHVGR

300
YLFSKSLEPG  SVEIAQISQY  CNLVSFVLFY

HELIX 7                          330
LSAAINPILY  NIMSKKYRVA  VFKLLGFEPF

353
SQRKLSTLKD  ESSRAWTESS  INT (SEQ ID NO:3)
```

FIG.3

```
                10        20        30        40
                 .         .         .         .
        GCAGCCTCTCACTTCCCTCTTTCCTCTCCTAGCATCCTCC    40
        CTGAGAGCCCGCGCTCGATACTCCTTTGCACTCTTTCGCG    80
        CCTAAGAGAACCTTCTCTGGGACCAGCCGGCTCCACCCTC   120
        TCGGTCCTATCCAAGAGCCAGTTAAGCAGAGCCCTAAGCA   160
        TGTGGAACGCGACCCCGAGCGAGGAACCGGGGCCCAACCT   200

210       220       230       240
                 .         .         .         .
        CACGCTGCCAGACCTGGGCTGGGACGCTCCCCCTGAAAAC   240
        GACTCGCTAGTGGAGGAGCTGCTGCCGCTCTTCCCCACGC   280
        CGCTGTTGGCGGGCGTCACCGCCACCTGCGTGGCGCTCTT   320
        CGTGGTGGGTATCGCGGGCAACCTGCTCACGATGCTGGTA   360
        GTGTCACGCTTCCGCGAGATGCGCACCACCACCAACCTCT   400

410       420       430       440
                 .         .         .         .
        ACCTGTCCAGCATGGCCTTCTCCGACCTACTCATCTTCCT   440
        CTGCATGCCCCTCGACCTCTTCCGCCTTTGGCAGTACCGG   480
        CCTTGGAACCTTGGCAACCTGCTCTGCAAACTCTTCCAGT   520
        TCGTTAGCGAGAGCTGCACCTACGCCACAGTGCTCACCAT   560
        CACCGCGCTGAGCGTCGAGCGCTACTTCGCCATCTGCTTC   600

610       620       630       640
                 .         .         .         .
        CCGCTGCGGGCCAAGGTAGTGGTCACCAAGGGCCGGGTAA   640
        AGCTGGTCATCCTGGTCATCTGGGCCGTGGCCTTCTGCAG   680
        CGCCGGGCCCATCTTCGTGCTGGTCGGAGTGGAGCATGAT   720
        AACGGCACTGACCCTCGGGACACCAACGAGTGCCGCGCCA   760
        CGGAGTTCGCCGTGCGCTCCGGGCTGCTTACCGTCATGGT   800

810       820       830       840
                 .         .         .         .
        CTGGGTGTCCAGTGTCTTCTTCTTCCTGCCTGTCTTCTGC   840
        CTCACTGTGCTCTATAGCCTCATCGGCAGGAAGCTCTGGC   880
        GGAGGAAGCGCGGCGAGGCGGCGGTGGGCTCCTCGCTCAG   920
        GGACCAGAACCACAAACAAACCGTGAAAATGCTGGGTGGG   960
        TCTCAATGCGCCCTCGAGCTTTCTCTCCCGGGTCCCCTCC  1000

1010      1020      1030      1040
                 .         .         .         .
        ACTCCTCGTGCCTTTTCTCTTCTCCCTGA  1029 (SEQ ID NO:4)
```

FIG.4

```
           10         20         30         40
MWNATPSEEP GPNLTLPDLG WDAPPENDSL VEELLPLFPT  40
PLLAGVTATC VALFVVGIAG NLLTMLVVSR FREMRTTTNL  80
YLSSMAFSDL LIFLCMPLDL FRLWQYRPWN LGNLLCKLFQ 120
FVSESCTYAT VLTITALSVE RYFAICFPLR AKVVVTKGRV 160
KLVILVIWAV AFCSAGPIFV LVGVEHDNGT DPRDTNECRA 200

210        220        230        240
TEFAVRSGLL TVMVWVSSVF FFLPVFCLTV LYSLIGRKLW 240
RRKRGEAAVG SSLRDQNHKQ TVKMLGGSQC ALELSLPGPL 280
HSSCLFSSP  289 (SEQ ID NO:5)
```

FIG. 5

```
        10        20        30        40
CGCCCAGCGAAGAGCCGGGGTTCAACCTCACACTGGCCGA    40
CCTGGACTGGGATGCTTCCCCCGGCAACGACTCGCTGGGC    80
GACGAGCTGCTGCAGCTCTTCCCCGCGCCGCTGCTGGCGG   120
GCGTCACAGCCACCTGCGTGGCACTCTTCGTGGTGGGTAT   160
CGCTGGCAACCTGCTCACCATGCTGGTGGTGTCGCGCTTC   200

210       220       230       240
CGCGAGCTGCGCACCACCACCAACCTCTACCTGTCCAGCA   240
TGGCCTTCTCCGATCTGCTCATCTTCCTCTGCATGCCCCT   280
GGACCTCGTTCGCCTCTGGCAGTACCGGCCCTGGAACTTC   320
GGCGACCTCCTCTGCAAACTCTTCCAATTCGTCAGTGAGA   360
GCTGCACCTACGCCACGGTGCTCACCATCACAGCGCTGAG   400

410       420       430       440
CGTCGAGCGCTACTTCGCCATCTGCTTCCCACTCCGGGCC   440
AAGGTGGTGGTCACCAAGGGGCGGGTGAAGCTGGTCATCT   480
TCGTCATCTGGGCCGTGGCCTTCTGCAGCGCCGGGCCCAT   520
CTTCGTGCTAGTCGGGGTGGAGCACGAGAACGGCACCGAC   560
CCTTGGGACACCAACGAGTGCCGCCCCACCGAGTTTGCGG   600

610       620       630       640
TGCGCTCTGGACTGCTCACGGTCATGGTGTGGGTGTCCAG   640
CATCTTCTTCTTCCTTCCTGTCTTCTGTCTCACGGTCCTC   680
TACAGTCTCATCGGCAGGAAGCTGTGGCGGAGGAGGCGCG   720
GCGATGCTGTCGTGGGTGCCTCGCTCAGGGACCAGAACCA   760
CAAGCAAACCGTGAAAATGCTGGCTGTAGTGGTGTTTGCC   800

810       820       830       840
TTCATCCTCTGCTGGCTCCCCTTCCACGTAGGGCGATATT   840
TATTTTCCAAATCCTTTGAGCCTGGCTCCTTGGAGATTGC   880
TCAGATCAGCCAGTACTGCAACCTCGTGTCCTTTGTCCTC   920
TTCTACCTCAGTGCTGCCATCAACCCCATTCTGTACAACA   960
TCATGTCCAAGAAGTACCGGGTGGCAGTGTTCAGACTTCT  1000

1010      1020      1030      1040
GGGATTCGAACCCTTCTCCCAGAGAAAGCTCTCCACTCTG  1040
AAAGATGAAAGTTCTCGGGCCTGGACAGAATCTAGTATTA  1080
ATACATGA  1088 (SEQ ID NO:6)
```

FIG. 6

```
              10           20
MLVVSRFREL   RTTTNLYLSS    20
MAFSDLLIFL   CMPLDLVRLW    40
QYRPWNFGDL   LCKLFQFVSE    60
SCTYATVLTI   TALSVERYFA    80
ICFPLRAKVV   VTKGRVKLVI   100

110          120
FVIWAVAFCS   AGPIFVLVGV   120
EHENGTDPWD   TNECRPTEFA   140
VRSGLLTVMV   WVSSIFFFLP   160
VFCLTVLYSL   IGRKLWRRRR   180
GDAVVGASLR   DQNHKQTVKM   200

210          220
LAVVVFAFIL   CWLPFHVGRY   220
LFSKSFEPGS   LEIAQISQYC   240
NLVSFVLFYL   SAAINPILYN   260
IMSKKYRVAV   FRLLGFEPFS   280
QRKLSTLKDE   SSRAWTESSI   300

310          320
NT   302 (SEQ ID NO:7)
```

FIG. 7

```
  1                                    30
PSEEPGFNLT  LADLDWDASP  GNDSLGDELL

HELIX 1    60
QLFPAP|LLAG  VTATCVALFV  VGIAGNLLTM|

HELIX 2    90
|L|VVSRFRELR  |TTTNLYLSSM  AFSDLLIFL|C

120
MPLDLVRLWQ  YRPWNFGDLL  CK|LFQFVSES

HELIX 3                            150
CTYATVLTIT  ALSV(ERY)FAI  CFPLRAKVVV|

HELIX 4   180
TKGRVK|LVIF  VIWAVAFCSA  GPIFVLVGV|E

210
HENGTDPWDT  NECRPTEFAV  R|SGLLTVMVW

HELIX 5                     240
VSSIFFFLPV  FCLTVLYSLI  G|RKLWRRRRG

HELIX 6  270
DAVVGASLRD  QNHKQT|VKML  AVVVFAFILC

300
WLPFHVG|RYL  FSKSFEPGSL  EIAQISQYCN

HELIX 7                     330
|LVSFVLFYLS  AAINPILYNI  MS|KKYRVAVF

360
RLLGFEPFSQ  RKLSTLKDES  SRAWTESSIN

361
T  (SEQ ID NO:8)
```

FIG.8

```
                      10        20        30        40
                       .         .         .         .
           GCGCCTCACGCTCCCGCTTCGCGGCGCCTGGTCCCTGCGG    40
           TCCCCACTCGCTGCGACGCTTTGGGAAGTGCGAGATGGAA    80
           CTGGATCGAGAACGCAAATGCGAGGCAGGGCTGGTGACAG   120
           CATCCTCCCTACGCGTCTGCACCCGCTCCTCCCTCGCACC   160
           CTCCCGCGCCTAAGCGGACCTCCTCGGGAGCCAGCTCGGT   200

210       220       230       240
                       .         .         .         .
           CCAGCCTCCCAGCGCAGTCACGTCCCAGAGCCTGTTCAGC   240
           TGAGCCGGCAGCATGTGGAACGCGACGCCCAGCGAAGAGC   280
           CGGGGTTCAACCTCACACTGGCCGACCTGGACTGGGATGC   320
           TTCCCCCGGCAACGACTCGCTGGGCGACGAGCTGCTGCAG   360
           CTCTTCCCCGCGCCGCTGCTGGCGGGCGTCACAGCCACCT   400

410       420       430       440
                       .         .         .         .
           GCGTGGCACTCTTCGTGGTGGGTATCGCTGGCAACCTGCT   440
           CACCATGCTGGTGGTGTCGCGCTTCCGCGAGCTGCGCACC   480
           ACCACCAACCTCTACCTGTCCAGCATGGCCTTCTCCGATC   520
           TGCTCATCTTCCTCTGCATGCCCCTGGACCTCGTTCGCCT   560
           CTGGCAGTACCGGCCCTGGAACTTCGGCGACCTCCTCTGC   600

610       620       630       640
                       .         .         .         .
           AAACTCTTCCAATTCGTCAGTGAGAGCTGCACCTACGCCA   640
           CGGTGCTCACCATCACAGCGCTGAGCGTCGAGCGCTACTT   680
           CGCCATCTGCTTCCCACTCCGGGCCAAGGTGGTGGTCACC   720
           AAGGGGCGGGTGAAGCTGGTCATCTTCGTCATCTGGGCCG   760
           TGGCCTTCTGCAGCGCCGGGCCCATCTTCGTGCTAGTCGG   800

810       820       830       840
                       .         .         .         .
           GGTGGAGCACGAGAACGGCACCGACCCTTGGGACACCAAC   840
           GAGTGCCGCCCCACCGAGTTTGCGGTGCGCTCTGGACTGC   880
           TCACGGTCATGGTGTGGGTGTCCAGCATCTTCTTCTTCCT   920
           TCCTGTCTTCTGTCTCACGGTCCTCTACAGTCTCATCGGC   960
           AGGAAGCTGTGGCGGAGGAGGCGCGGCGATGCTGTCGTGG  1000
```

FIG.9A

```
          1010          1020          1030          1040
           .             .             .             .
GTGCCTCGCTCAGGGACCAGAACCACAAGCAAACCGTGAA   1040
AATGCTGGGTGGGTCTCAGCGCGCGCTCAGGCTTTCTCTC   1080
GCGGGTCCTATCCTCTCCCTGTGCCTTCTCCCTTCTCTCT   1120
GA   1122 (SEQ ID NO:9)
```

FIG.9B

```
          10        20        30        40
           .         .         .         .
    MWNATPSEEPGFNLTLADLDWDASPGNDSLGDELLQLFPA    40
    PLLAGVTATCVALFVVGIAGNLLTMLVVSRFRELRTTTNL    80
    YLSSMAFSDLLIFLCMPLDLVRLWQYRPWNFGDLLCKLFQ   120
    FVSESCTYATVLTITALSVERYFAICFPLRAKVVVTKGRV   160
    KLVIFVIWAVAFCSAGPIFVLVGVEHENGTDPWDTNECRP   200

210       220       230       240
           .         .         .         .
    TEFAVRSGLLTVMVWVSSIFFFLPVFCLTVLYSLIGRKLW   240
    RRRRGDAVVGASLRDQNHKQTVKMLGGSQRALRLSLAGPI   280
    LSLCLLPSL   289 (SEQ ID NO:10)
```

FIG.10

```
          10        20        30        40
           .         .         .         .
    MPLDLVRLWQYRPWNFGDLLCKLFQFVSESCTYATVLTIT    40
    ALSVERYFAICFPLRAKVVVTKGRVKLVIFVIWAVAFCSA    80
    GPIFVLVGVEHENGTDPWDTNECRPTEFAVRSGLLTVMVW   120
    VSSIFFFLPVFCLTVLYSLIGRKLWRRRRGDAVVGASLRD   160
    QNHKQTVKMLAVVVFAFILCWLPFHVGRYLFSKSFEPGSL   200

210       220       230       240
           .         .         .         .
    EIAQISQYCNLVSFVLFYLSAAINPILYNIMSKKYRVAVF   240
    RLLGFEPFSQRKLSTLKDESSRAWTESSINT   271 (SEQ ID NO:12)
```

FIG.12

```
              10        20        30        40
               .         .         .         .
         ATCTGCTCATCTTCCTCTGCATGCCCCTGGACCTCGTTCG    40
         CCTCTGGCAGTACCGGCCCTGGAACTTCGGCGACCTCCTC    80
         TGCAAACTCTTCCAATTCGTCAGTGAGAGCTGCACCTACG   120
         CCACGGTGCTCACCATCACAGCGCTGAGCGTCGAGCGCTA   160
         CTTCGCCATCTGCTTCCCACTCCGGGCCAAGGTGGTGGTC   200

210       220       230       240
               .         .         .         .
         ACCAAGGGGCGGGTGAAGCTGGTCATCTTCGTCATCTGGG   240
         CCGTGGCCTTCTGCAGCGCCGGGCCCATCTTCGTGCTAGT   280
         CGGGGTGGAGCACGAGAACGGCACCGACCCTTGGGACACC   320
         AACGAGTGCCGCCCCACCGAGTTTGCGGTGCGCTCTGGAC   360
         TGCTCACGGTCATGGTGTGGGTGTCCAGCATCTTCTTCTT   400

410       420       430       440
               .         .         .         .
         CCTTCCTGTCTTCTGTCTCACGGTCCTCTACAGTCTCATC   440
         GGCAGGAAGCTGTGGCGGAGGAGGCGCGGCGATGCTGTCG   480
         TGGGTGCCTCGCTCAGGGACCAGAACCACAAGCAAACCGT   520
         GAAAATGCTGGCTGTAGTGGTGTTTGCCTTCATCCTCTGC   560
         TGGCTCCCCTTCCACGTAGGGCGATATTTATTTTCCAAAT   600

610       620       630       640
               .         .         .         .
         CCTTTGAGCCTGGCTCCTTGGAGATTGCTCAGATCAGCCA   640
         GTACTGCAACCTCGTGTCCTTTGTCCTCTTCTACCTCAGT   680
         GCTGCCATCAACCCCATTCTGTACAACATCATGTCCAAGA   720
         AGTACCGGGTGGCAGTGTTCAGACTTCTGGGATTCGAACC   760
         CTTCTCCCAGAGAAAGCTCTCCACTCTGAAAGATGAAAGT   800

810       820       830       840
               .         .         .         .
         TCTCGGGCCTGGACAGAATCTAGTATTAATACATGA   836 (SEQ ID NO:11)
```

FIG. 11

```
                                            v10          v20
FIG.3-SWINE TYPE I CLONE 7-3orf    LTLPDLGWDAPPENDSLVEE
                                   LTLPDLGWDAPPENDSLVEE
FIG.5-SWINE TYPE II CLONE 1375m    LTLPDLGWDAPPENDSLVEE
                                          ^20          ^30
                                            v30          v40
FIG.3-SWINE TYPE I CLONE 7-3orf    LLPLFPTPLLAGVTATCVAL
                                   LLPLFPTPLLAGVTATCVAL
FIG.5-SWINE TYPE II CLONE 1375m    LLPLFPTPLLAGVTATCVAL
                                          ^40          ^50
                                            v50          v60
FIG.3-SWINE TYPE I CLONE 7-3orf    FVVGIAGNLLTMLVVSRFRE
                                   FVVGIAGNLLTMLVVSRFRE
FIG.5-SWINE TYPE II CLONE 1375m    FVVGIAGNLLTMLVVSRFRE
                                          ^60          ^70
                                            v70          v80
FIG.3-SWINE TYPE I CLONE 7-3orf    MRTTTNLYLSSMAFSDLLIF
                                   MRTTTNLYLSSMAFSDLLIF
FIG.5-SWINE TYPE II CLONE 1375m    MRTTTNLYLSSMAFSDLLIF
                                          ^80          ^90
                                            v90          v100
FIG.3-SWINE TYPE I CLONE 7-3orf    LCMPLDLFRLWQYRPWNLGN
                                   LCMPLDLFRLWQYRPWNLGN
FIG.5-SWINE TYPE II CLONE 1375m    LCMPLDLFRLWQYRPWNLGN
                                          ^100         ^110
                                            v110         v120
FIG.3-SWINE TYPE I CLONE 7-3orf    LLCKLFQFVSESCTYATVLT
                                   LLCKLFQFVSESCTYATVLT
FIG.5-SWINE TYPE II CLONE 1375m    LLCKLFQFVSESCTYATVLT
                                          ^120         ^130
                                            v130         v140
FIG.3-SWINE TYPE I CLONE 7-3orf    ITALSVERYFAICFPLRAKV
                                   ITALSVERYFAICFPLRAKV
FIG.5-SWINE TYPE II CLONE 1375m    ITALSVERYFAICFPLRAKV
                                          ^140         ^150
                                            v150         v160
FIG.3-SWINE TYPE I CLONE 7-3orf    VVTKGRVKLVILVIWAVAFC
                                   VVTKGRVKLVILVIWAVAFC
FIG.5-SWINE TYPE II CLONE 1375m    VVTKGRVKLVILVIWAVAFC
                                          ^160         ^170
```

FIG.13A

```
                                                  v170        v180
FIG.3-SWINE TYPE I  CLONE 7-3orf    SAGPIFVLVGVEHDNGTDPR
                                    SAGPIFVLVGVEHDNGTDPR
FIG.5-SWINE TYPE II CLONE 1375m     SAGPIFVLVGVEHDNGTDPR
                                          ^180        ^190
                                                  v190        v200
FIG.3-SWINE TYPE I  CLONE 7-3orf    DTNECRATEFAVRSGLLTVM
                                    DTNECRATEFAVRSGLLTVM
FIG.5-SWINE TYPE II CLONE 1375m     DTNECRATEFAVRSGLLTVM
                                          ^200        ^210
                                                  v210        v220
FIG.3-SWINE TYPE I  CLONE 7-3orf    VWVSSVFFFLPVFCLTVLYS
                                    VWVSSVFFFLPVFCLTVLYS
FIG.5-SWINE TYPE II CLONE 1375m     VWVSSVFFFLPVFCLTVLYS
                                          ^220        ^230
                                                  v230        v240
FIG.3-SWINE TYPE I  CLONE 7-3orf    LIGRKLWRRKRGEAAVGSSL
                                    LIGRKLWRRKRGEAAVGSSL
FIG.5-SWINE TYPE II CLONE 1375m     LIGRKLWRRKRGEAAVGSSL
                                          ^240        ^250
                                                  v250        v260
FIG.3-SWINE TYPE I  CLONE 7-3orf    RDQNHKQTVKMLAVVVFAFI
                                    RDQNHKQTVKML:     A:
FIG.5-SWINE TYPE II CLONE 1375m     RDQNHKQTVKMLGGSQCALE
                                          ^260        ^270
                                                  v270
FIG.3-SWINE TYPE I  CLONE 7-3orf    LCWL-PFHVGRYLFSKS (SEQ ID NO:3)
                                    L.   P:H :..LFS.:
FIG.5-SWINE TYPE II CLONE 1375m     LSLPGPLH-SSCLFSSP (SEQ ID NO:5)
                                          ^280
```

FIG.13B

```
                                                    v10         v20
FIG.8-HUMAN TYPE I 1146orf        PSEEPGFNLTLADLDWDASP
                                  PSEEPGFNLTLADLDWDASP
FIG.10-HUMAN TYPE II CLONE1141m   PSEEPGFNLTLADLDWDASP
                                         ^10         ^20
                                                    v30         v40
FIG.8-HUMAN TYPE I 1146orf        GNDSLGDELLQLFPAPLLAG
                                  GNDSLGDELLQLFPAPLLAG
FIG.10-HUMAN TYPE II CLONE1141m   GNDSLGDELLQLFPAPLLAG
                                         ^30         ^40
                                                    v50         v60
FIG.8-HUMAN TYPE I 1146orf        VTATCVALFVVGIAGNLLTM
                                  VTATCVALFVVGIAGNLLTM
FIG.10-HUMAN TYPE II CLONE1141m   VTATCVALFVVGIAGNLLTM
                                         ^50         ^60
                                                    v70         v80
FIG.8-HUMAN TYPE I 1146orf        LVVSRFRELRTTTNLYLSSM
                                  LVVSRFRELRTTTNLYLSSM
FIG.10-HUMAN TYPE II CLONE1141m   LVVSRFRELRTTTNLYLSSM
                                         ^70         ^80
                                                    v90         v100
FIG.8-HUMAN TYPE I 1146orf        AFSDLLIFLCMPLDLVRLWQ
                                  AFSDLLIFLCMPLDLVRLWQ
FIG.10-HUMAN TYPE II CLONE1141m   AFSDLLIFLCMPLDLVRLWQ
                                         ^90         ^100
                                                    v110        v120
FIG.8-HUMAN TYPE I 1146orf        YRPWNFGDLLCKLFQFVSES
                                  YRPWNFGDLLCKLFQFVSES
FIG.10-HUMAN TYPE II CLONE1141m   YRPWNFGDLLCKLFQFVSES
                                         ^100        ^110
                                                    v130        v140
FIG.8-HUMAN TYPE I 1146orf        CTYATVLTITALSVERYFAI
                                  CTYATVLTITALSVERYFAI
FIG.10-HUMAN TYPE II CLONE1141m   CTYATVLTITALSVERYFAI
                                         ^130        ^140 v150        v160
FIG.8-HUMAN TYPE I 1146orf        CFPLRAKVVVTKGRVKLVIF
                                  CFPLRAKVVVTKGRVKLVIF
FIG.10-HUMAN TYPE II CLONE1141m   CFPLRAKVVVTKGRVKLVIF
                                         ^150        ^160
```

FIG.14A

```
                                           v170        v180
                                   VIWAVAFCSAGPIFVLVGVE
FIG.8-HUMAN TYPE I 1146orf         VIWAVAFCSAGPIFVLVGVE
FIG.10-HUMAN TYPE II CLONE1141m    VIWAVAFCSAGPIFVLVGVE
                                           ^170        ^180 v190        v200
                                   HENGTDPWDTNECRPTEFAV
FIG.8-HUMAN TYPE I 1146orf         HENGTDPWDTNECRPTEFAV
FIG.10-HUMAN TYPE II CLONE1141m    HENGTDPWDTNECRPTEFAV
                                           ^190        ^200 v210        v220
                                   RSGLLTVMVWVSSIFFFLPV
FIG.8-HUMAN TYPE I 1146orf         RSGLLTVMVWVSSIFFFLPV
FIG.10-HUMAN TYPE II CLONE1141m    RSGLLTVMVWVSSIFFFLPV
                                           ^210        ^220 v230        v240
                                   FCLTVLYSLIGRKLWRRRRG
FIG.8-HUMAN TYPE I 1146orf         FCLTVLYSLIGRKLWRRRRG
FIG.10-HUMAN TYPE II CLONE1141m    FCLTVLYSLIGRKLWRRRRG
                                           ^230        ^240 v250        v260
                                   DAVVGASLRDQNHKQTVKML (SEQ ID NO:8)
FIG.8-HUMAN TYPE I 1146orf         DAVVGASLRDQNHKQTVKML
FIG.10-HUMAN TYPE II CLONE1141m    DAVVGASLRDQNHKQTVKML (SEQ ID NO:10)
                                           ^250        ^260
```

FIG.14B

```
                                            v10        v20        v30        v40
FIG.3-SWINE TYPE I CLONE 7-3orf   LTLPDLGWDAPPENDSLVEELLPLFPTPLLAGVTATCVAL
                                  LTL:DL:WDA:P.NDSL :ELL.LFP:PLLAGVTATCVAL
FIG.8-HUMAN TYPE I 1146orf        LTLADLDWDASPGNDSLGDELLQLFPAPLLAGVTATCVAL
                                            ^10        ^20        ^30        ^40
                                            v50        v60        v70        v80
FIG.3-SWINE TYPE I CLONE 7-3orf   FVVGIAGNLLTMLVVSRFREMRTTTNLYLSSMAFSDLLIF
                                  FVVGIAGNLLTMLVVSRFRE:RTTTNLYLSSMAFSDLLIF
FIG.8-HUMAN TYPE I 1146orf        FVVGIAGNLLTMLVVSRFRELRTTTNLYLSSMAFSDLLIF
                                            ^50        ^60        ^70        ^80
                                            v90       v100       v110       v120
FIG.3-SWINE TYPE I CLONE 7-3orf   LCMPLDLFRLWQYRPWNLGNLLCKLFQFVSESCTYATVLT
                                  LCMPLDL RLWQYRPWN:G:LLCKLFQFVSESCTYATVLT
FIG.8-HUMAN TYPE I 1146orf        LCMPLDLVRLWQYRPWNFGDLLCKLFQFVSESCTYATVLT
                                            ^90       ^100       ^110       ^120
                                           v130       v140       v150       v160
FIG.3-SWINE TYPE I CLONE 7-3orf   ITALSVERYFAICFPLRAKVVVTKGRVKLVILVIWAVAFC
                                  ITALSVERYFAICFPLRAKVVVTKGRVKLVI:VIWAVAFC
FIG.8-HUMAN TYPE I 1146orf        ITALSVERYFAICFPLRAKVVVTKGRVKLVIFVIWAVAFC
                                           ^130       ^140       ^150       ^160
                                           v170       v180       v190       v200
FIG.3-SWINE TYPE I CLONE 7-3orf   SAGPIFVLVGVEHDNGTDPRDTNECRATEFAVRSGLLTVM
                                  SAGPIFVLVGVEH:NGTDP:DTNECR:TEFAVRSGLLTVM
FIG.8-HUMAN TYPE I 1146orf        SAGPIFVLVGVEHENGTDPWDTNECRPTEFAVRSGLLTVM
                                           ^170       ^180       ^190       ^200
                                           v210       v220       v230       v240
FIG.3-SWINE TYPE I CLONE 7-3orf   VWVSSVFFFLPVFCLTVLYSLIGRKLWRRKRGEAAVGSSL
                                  VWVSS:FFFLPVFVLTVLYSLIGRKLWRR:RG:A.VG:SL
FIG.8-HUMAN TYPE I 1146orf        VWVSSIFFFLPVFCLTVLYSLIGRKLWRRRRGDAVVGASL
                                           ^210       ^220       ^230       ^240
                                           v250       v260       v270       v280
FIG.3-SWINE TYPE I CLONE 7-3orf   RDQNHKQTVKMLAVVVFAFILCWLPFHVGRYLFSKSLEPG
                                  RDQNHKQTVKMLAVVVFAFILCWLPFHVGRYLFSKS:EPG
FIG.8-HUMAN TYPE I 1146orf        RDQNHKQTVKMLAVVVFAFILCWLPFHVGRYLFSKSFEPG
                                           ^250       ^260       ^270       ^280
                                           v290       v300       v310       v320
FIG.3-SWINE TYPE I CLONE 7-3orf   SVEIAQISQYCNLVSFVLFYLSAAINPILYNIMSKKYRVA
                                  S:EIAQISQYCNLVSFVLFYLSAAINPILYNIMSKKYRVA
FIG.8-HUMAN TYPE I 1146orf        SLEIAQISQYCNLVSFVLFYLSAAINPILYNIMSKKYRVA
                                           ^290       ^300       ^310       ^320
                                           v330       v340       v350
FIG.3-SWINE TYPE I CLONE 7-3orf   VFKLLGFEPFSQRKLSTLKDESSRAWTESSINT (SEQ ID NO:3)
                                  VF:LLGFEPFSQRKLSTLKDESSRAWTESSINT
FIG.8-HUMAN TYPE I 1146orf        VFRLLGFEPFSQRKLSTLKDESSRAWTESSINT (SEQ ID NO:8)
                                           ^330       ^340       ^350       ^360
```

FIG.15

|  | v10 v20 |
|---|---|
| FIG.5-SWINE TYPE II CLONE 1375m | MWNATPSEEPGPNLTLPDLG |
|  | MWNATPSEEPG NLTL:DL: |
| FIG.10-HUMAN TYPE II CLONE1141m | MWNATPSEEPGFNLTLADLD |
|  | ^10 ^20 |
|  | v30 v40 |
| FIG.5-SWINE TYPE II CLONE 1375m | WDAPPENDSLVEELLPLFPT |
|  | WDA:P.NDSL :ELL.LFP: |
| FIG.10-HUMAN TYPE II CLONE1141m | WDASPGNDSLGDELLQLFPA |
|  | ^30 ^40 |
|  | v50 v60 |
| FIG.5-SWINE TYPE II CLONE 1375m | PLLAGVTATCVALFVVGIAG |
|  | PLLAGVTATCVALFVVGIAG |
| FIG.10-HUMAN TYPE II CLONE1141m | PLLAGVTATCVALFVVGIAG |
|  | ^50 ^60 |
|  | v70 v80 |
| FIG.5-SWINE TYPE II CLONE 1375m | NLLTMLVVSRFREMRTTTNL |
|  | NLLTMLVVSRFRE:RTTTNL |
| FIG.10-HUMAN TYPE II CLONE1141m | NLLTMLVVSRFRELRTTTNL |
|  | ^70 ^80 |
|  | v90 v100 |
| FIG.5-SWINE TYPE II CLONE 1375m | YLSSMAFSDLLIFLCMPLDL |
|  | YLSSMAFSDLLIFLCMPLDL |
| FIG.10-HUMAN TYPE II CLONE1141m | YLSSMAFSDLLIFLCMPLDL |
|  | ^90 ^100 |
|  | v110 v120 |
| FIG.5-SWINE TYPE II CLONE 1375m | FRLWQYRPWNLGNLLCKLFQ |
|  | RLWQYRPWN:G:LLCKLFQ |
| FIG.10-HUMAN TYPE II CLONE1141m | VRLWQYRPWNFGDLLCKLFQ |
|  | ^110 ^120 |
|  | v130 v140 |
| FIG.5-SWINE TYPE II CLONE 1375m | FVSESCTYATVLTITALSVE |
|  | FVSESCTYATVLTITALSVE |
| FIG.10-HUMAN TYPE II CLONE1141m | FVSESCTYATVLTITALSVE |
|  | ^130 ^140 |
|  | v150 v160 |
| FIG.5-SWINE TYPE II CLONE 1375m | RYFAICFPLRAKVVVTKGRV |
|  | RYFAICFPLRAKVVVTKGRV |
| FIG.10-HUMAN TYPE II CLONE1141m | RYFAICFPLRAKVVVTKGRV |
|  | ^150 ^160 |

FIG.16A

```
                                              v170         v180
FIG.5-SWINE TYPE II CLONE 1375m    KLVILVIWAVAFCSAGPIFV
                                   KLVI:VIWAVAFCSAGPIFV
FIG.10-HUMAN TYPE II CLONE1141m    KLVIFVIWAVAFCSAGPIFV
                                              ^170         ^180
                                              v190         v200
FIG.5-SWINE TYPE II CLONE 1375m    LVGVEHDNGTDPRDTNECRA
                                   LVGVEH:NGTDP:DTNECR:
FIG.10-HUMAN TYPE II CLONE1141m    LVGVEHENGTDPWDTNECRP
                                              ^190         ^200
                                              v210         v220
FIG.5-SWINE TYPE II CLONE 1375m    TEFAVRSGLLTVMVWVSSVF
                                   TEFAVRSGLLTVMVWVSS:F
FIG.10-HUMAN TYPE II CLONE1141m    TEFAVRSGLLTVMVWVSSIF
                                              ^210         ^220
                                              v230         v240
FIG.5-SWINE TYPE II CLONE 1375m    FFLPVFCLTVLYSLIGRKLW
                                   FFLPVFCLTVLYSLIGRKLW
FIG.10-HUMAN TYPE II CLONE1141m    FFLPVFCLTVLYSLIGRKLW
                                              ^230         ^240
                                              v250         v260
FIG.5-SWINE TYPE II CLONE 1375m    RRKRGEAAVGSSLRDQNHKQ
                                   RR:RG:A.VG:SLRDQNHKQ
FIG.10-HUMAN TYPE II CLONE1141m    RRRRGDAVVGASLRDQNHKQ
                                              ^250         ^260
                                              v270         v280
FIG.5-SWINE TYPE II CLONE 1375m    TVKMLGGSQCALELSLPGPL
                                   TVKMLGGSQ AL LSL:GP:
FIG.10-HUMAN TYPE II CLONE1141m    TVKMLGGSQRALRLSLAGPI
                                              ^270         ^280

FIG.5-SWINE TYPE II CLONE 1375m    HSSCLFSS (SEQ ID NO:5)
                                    S CL::S
FIG.10-HUMAN TYPE II CLONE1141m    LSLCLLPS (SEQ ID NO:10)
```

FIG.16B

| | SWINE CLONE 7-3 | | HUMAN CLONE 1146 | |
|---|---|---|---|---|
| | 24 HOURS | 48 HOURS | 24 HOURS | 48 HOURS |
| COMPOUND A (100 μm) (1000 nM) | 13,553 9,176 | 2,692 | 1,353 3,091 | 2,228 |
| COMPOUND B (100nM) COMPOUND C (100nM) | 717 100 | 425 58 3,839 1,806 | 113 96 | 108 67 |
| GHRP-2 (1000 nM) GHRP-6 (1000 nM) | 2,492 5,003 | | 1542 617 | |

```
  1  MWNATPSEEP GFNLTLADLD WDASPGNDSL GDELLQLFPA PLLAGVTATC

51  VALFVVGIAG NLLTMLVVSR FRELRTTTNL YLSSMAFSDL LIFLCMPLDL

101  VRLWQYRPWN FGDLLCKLFQ FVSESCTYAT VLTITALSVE RYFAICFPLR

151  AKVVVTKGRV KLVIFVIWAV AFCSAGPIFV LVGVEHENGT DPWDTNECRP

201  TEFAVRSGLL TVMVWVSSIF FFLPVFCLTV LYSLIGRKLW RRRRGDAVVG

251  ASLRDQNHKQ TVKMLAVVVF AFILCWLPFH VGRYLFSKSF EPGSLEIAQI

301  SQYCNLVSFV LFYLSAAINP ILYNIMSKKY RVAVFRLLGF EPFSQRKLST

351  LKDESSRAWT ESSINT* (SEQ ID NO:13)
```

FIG.22

```
         10           20           30           40           50           60
ATG TGG AAC GCG ACC CCC AGC GAG GAG CCT AAC GTC ACG TTG GAC CTG CCC GCT TGG        60
GAC GCT TCC CCC GGC AAC GAC TCA CTG GAC TTC GAC CTG TTC CCG CTG TTC CCG AAC       120
CTG CTG GCA GGC GTC ACC GCC GTG GCG CTC TGC CGC GCG CTC GTG GGC ATC ACC AGC       180
CTG CTC ACT ATG CTG GTG GTG TCC TTC CGC GAG CTG CGC ATC TTC CGC ACC ACC CTC TAC   240
CTG TCC AGC ATG GCC TTC GCC GAT CTG CTC ATC TTC CTG ATG CCG CTG ATG CCG CTC GTC   300

310          320          330          340          350          360
CGC CTC TGG CAG TAC CGG CCC TGG AAC TTC GGC GAC CTG CTC TGC AAA CTC TTC CAG TTT   360
GTC AGC GAG AGC TGC ACC TAC TGC CTC GTG ACG GTC CTC ACC ATC ACC GCG CTG AGC CGC   420
TAC TTC GCC ATC TGC TTC CCT CTG CGG GCC AAG GTG GTG AGC GTC ACT AAG GGC CGC CGC   480
CTG GTC ATC CTT GTC GCC ATC TGG GCC GTG TGC AGC GCG GGG CCC ATC TTC GTG CTG       540
GTG GGC GTG GAG CAC GAA AAC GGC ACA GAT CCC CGG GAC GAC AAC GAA TGC CGC GCC ACC   600

610          620          630          640          650          660
GAG TTC GCT GTG CGC TCT TGC GTC ATG GTG TGG GTG TCC AGC GTC TTC TTC                660
TTT CTA CCG GTC TTC TGC GTG CTC ACT GTG CTC TAC AGT CTC CGG GAC AAG CAC CTA TCG CGG   720
AGA CGC GGA GAT GCA GCG Ggt gag tcc tgg tcc cac ccg ctg acc ctg ttt ccc gcc ctt ccc   780
AAG ATG CTT Ggt gag ctt ctg ttt ctg ttt ctc atc tcc gct ccc caa gtc tct caa gtc tct   840
cag cgg cct cta                                                                    900
```

FIG.23A

```
       910         920         930         940         950         960
ttt ctc tgc ctc tct cac ctt ggt tct cgg tct tgc ttt ctg ttt tct tcc tgt ctt  960
ttc ctg tat ctt gtc cac gaa aaa gaa ccc tca tat tgg taa ttc ctt aaa acg agg aac 1020
ctt ggt ctg gga aaa ttg gtc caa gat gga aat acc tca cgg ttt att gag ccc cta att 1080
gtt aac ggt tta gct tct tgt ctc aca tag aat ttg tgg tta tca aag taa taa tat taa 1140
ggt aag cag gca ggt aat ggg ttt aga aat cac tcc atg gta agt cta acc aca aat ttg 1200

1210        1220        1230        1240        1250        1260
ggt cac tct gtt aag gac ggc tta tag atg tat ttt gtt tgt ttt caa tat tgg gat ttg 1260
ttt tct gcc ctg cat ctt tct gct ggg gtc cag ata att aca tcc ttt ttc ttg ttt tgc 1320
cag gag ggg ctt cat cat gct cat ggg gtc tcc ttc ctt tcc tca aac tgt cct cag taa 1380
tat agg cca gga tag ggt gga gaa tag gcc atc ctg ctt ccc caa agg cat gtg ctt tct 1440
ggg tac tga acg gtt act gca taa act gca taa act ctg ctt ccc caa agg ctt ggt gtg gta 1500

1510        1520        1530        1540        1550        1560
aag tca tga aga tgg tgc tca tgt cca aga gga acc tct gat ctc act ttt caa ggg att 1560
tca tgt ttg ctg aca ttt aat act tgt tag ttt ttg cag ggg gat gat ttc tca ttt gca 1620
att tta ttc tca tga ttt gca tgt cag aat gtt aga gat ttc tca ggg atg tca ggt 1680
tct gtt tcc aga tga gtg att gcc ctg tgt cct cca ttg gac tgt aaa ctc ata tgc acc 1740
aga cag ggt cta cat tgc cgt ggt gca tag cct tcc atg tgt cac tta gtc cta aag 1800

FIG.23B
```

```
           1810        1820        1830        1840        1850        1860
             .           .           .           .           .           .
aga agt tac taa cct aat ctc act aat ctc act ggc atc tca atg ccg atc cca ttg  1860
tca tct gaa aat ttg aag ggg aca tta aag tgg cac agg gac aat cag aat att ttt ctc  1920
tca ttg ctg aat ttt aaa aat cta aaa aat tgg aat tct tga aga aac tat ctt ata  1980
tga cta aaa tga agc ctt ggg tgg gtg cta att att gtc tgg ctt acc tgc ccc ccc  2040
cac tac tta tat ctt tta gag atg aca cag act tgc ttt ccc tgt ggc tac taa tcc caa  2100

2110        2120        2130        2140        2150        2160
             .           .           .           .           .           .
ttg cac att cag tcc ctt gat aga ctt act cta aaa atc taa gtt cag cgg tcc acg aaa  2160
cat aac aaa gcc tgt cct aaa aca gca aag aca aag gtc ttt ccc cat tcc cta aca tac  2220
gca aga aag aaa aga gaa aaa cag aag aac aag gtc ttt gtt tct gca tct tca gta tgc cca  2280
agg aat gga aat tat taa gtc tac gtg ata gcc aat gca tct tta ctg ggc atg ctt gac ccc  2340
caa ggg tgc tgc cgg agc cat tgc tca ggg ctg gag tat tta ctg ggc atg ctt gac ccc  2400

2410        2420        2430        2440        2450        2460
             .           .           .           .           .           .
agc atg gag ggt gag aag tgc tcc tgg gaa ctc tga tcc act gct gtg gtg gag agc aaa  2460
cac ctg gcc tca ttt ata ctt gtt gtc tgt ata atg ggg gga taa tca tta  2520
cta aac tgt tta gct gag cct cat gtc agt gtc caa tca caa agc aga att acc aca cag  2580
act ggg aag ctc agt gat gaa gat tgt cgg gtc tga cag ttg gtc tgt tgc gta tag  2640
tgt tag acc caa cgg agg cag tat tta toa gga ggg cag ggt tgt tcc atg ttt ccc gtg tta  2700
```

FIG.23C

```
        2710        2720        2730        2740        2750        2760
aag agc aag aga tga tgt ttg tca gta ggc atg cag ctc atg gtg aaa aga aag tcc aga  2760
ctt aaa gat gtg gtg tga aag tga ttt gtg ctt tgc ccc acc ctg gtc tct ctc tgt gtg cst  2820
tca GCT GTG GTG GTG TTT GCT TTC ATC CTC TGC TGG CTG CCC TTC CAC GTG GGA AGA TAC  2880
CTC TTT TCC AAG TCC TTC GAG CCT TTC TCT CTG GAG ATC GCT CAG ATC AGC CAG TAC TGC  2940
AAC CTG TCC GTG TCC TTT GTC CTC CTC TAC CTC AGC GCT ATC AAC CCC ATT CTG TAC AAC  3000

3010        3020        3030        3040        3050        3060
ATC ATG TCC AAG AAG TAC CGG GTG GCA GTG TTC AAA CTG CTA GGA TTT GAA TCC TTC TCC  3060
CAG AGA AAG CTT TCC ACT CTG AAG GAG AGT TCC CGG GCC TGG ACA AAG TCG AGC ATC  3120
AAC ACA TGA  3129 (SEQ ID NO:14)
```

FIG.23D

```
     10          20          30          40          50          60
ATG TGG AAC GCG ACC CCC AGC GAG GAG CCT AAC GTC CTG ACG TTG GAC CTG GAT TGG     60
GAC GCT TCC CCC GGC AAC GAC TCA CTG CCT GAA CTG CCG CTG TTC CCC GCT CCG        120
CTG CTG GCA GGC GTC ACC GCC GTC TGC ACC GCG CTC GTG GCG ATC TCA GGC AAC        180
CTG CTC ACT ATG CTG GTG GTG TCC CGC TTC CGC GAG CTG CGC CTG CGC AAC CTC TAC    240
CTG TCC AGC ATG GCC TTC TCG GAT CTG ATC TTC CTG TGC CCG CTG GAC CTC GTC        300

310         320         330         340         350         360
CGC CTC TGG CAG TAC CGG CCC TGG AAC TTC GGC GAC CTG CTC TTC CAG TTT           360
GTC ACC GAG AGC TGC ACC TAC TGC CTG CTG CGG GCC AAG GTG GTC AGC CTG GAG CGC    420
TAC TTC GCC ATC TGC TTC CCT CTG GCC GGT GTG TGC ACT AAG GGC CGC GTG AAG       480
CTG GTC ATC CTT GTC ATC GAA CAC GGG ACA AAC TTC CCC AGC GCG ACC ATC TTC GTG CTG 540
GTG GGC GTG GAG CAC GGC CTG ACG TGC CGG GAC GAC AAC TGC CGC GCC ACC           600

610         620         630         640         650         660
GAG TTC GCT GTG CGC TCT GGG CTG CGC ACC GTC ATG GTG TGG TCC AGC GTC TTC TTC    660
TTT CTA CCG GTC TTC TGC CTC ACT GTG CTG CGG GAC CTC ATC GGG AAC AGG AAG CTA TGG CGG    720
AGA CGC GGA GAT GCA GCG GTG GCC GTG CTC CGG GAC CAG CAG AAG CAC AAG CAG ACA GTG      780
AAG ATG CTT GCT GTG GTG GTG TTT GCT CTC ATC CTC TGC TGG CTG CCC TTC CAC ATC GGA    840
AGA TAC CTC TTT TCC AAG TCC TTC GAG CCT GGC TCT CTG GAG ATC GCT CAG AGC CAG    900
```

FIG.24A

```
                    910         920         930         940         950         960
TAC TGC AAC CTG GTG TCC TTT GTC CTC TTC TAC CTC AGC GCT GCC ATC AAC CCC ATT CTG    960
TAC AAC ATC ATG TCC AAG AAG TAC CGG GTG GCA GTG TTC AAA CTG CTA GGA TTT GAA TCC   1020
TTC TCC CAG AGA AAG CTT TCC ACT CTG AAG GAT GAG AGT TCC CGG GCC TGG ACA AAG TCG   1080
AGC ATC AAC ACA 1092 (SEQ ID NO:15)
```

FIG.24B

```
            10         20         30         40         50
            .          .          .          .          .
MWNATPSEEP  EPNVTLDLDW DASPGNDSLP DELLPLFPAP LLAGVTATCV   50
ALFVVGISGN  LLTNLVVSRF RELRTTTNLY LSSMAFSDLL IFLCMPLDLV  100
RLWQYRPWNF  GDLLCKLFQF VSESCTYATV LTITALSVER YFAICFPLRA  150
KVVVTKGRVK  LVILVIWAVA FCSAGPIFVL VGVEHENGTD PRDTNECRAT  200
EFAVRSGLLT  VMVWVSSVFF FLPVFCLTVL YSLIGRKLWR RRGDAAVGAS  250

260        270        280        290        300
            .          .          .          .          .
LRDQNHKQTV  KMLAVVVFAF ILCWLPFHVG RYLFSKSFEP GSLEIAQISQ  300
YCNLVSFVLF  YLSAAINPIL YNIMSKKYRV AVFKLLGFES FSQRKLSTLK  350
DESSRAWTKS  SINT    364 (SEQ ID NO:16)
```

FIG.25

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1063 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CCTCACGCTG CCAGACCTGG GCTGGGACGC TCCCCCTGAA AACGACTCGC TAGTGGAGGA     60
GCTGCTGCCG CTCTTCCCCA CGCCGCTGTT GGCGGGCGTC ACCGCCACCT GCGTGGCGCT    120
CTTCGTGGTG GGTATCGCGG GCAACCTGCT CACGATGCTG GTAGTGTCAC GCTTCCGCGA    180
GATGCGCACC ACCACCAACC TCTACCTGTC CAGCATGGCC TTCTCCGACC TACTCATCTT    240
CCTCTGCATG CCCCTCGACC TCTTCCGCCT CTGGCAGTAC CGGCCTTGGA ACCTTGGCAA    300
CCTGCTCTGC AAACTCTTCC AGTTCGTTAG CGAGAGCTGC ACCTACGCCA CAGTGCTCAC    360
CATCACCGCG CTGAGCGTCG AGCGCTACTT CGCCATCTGC TTCCCGCTGC GGGCCAAGGT    420
AGTGGTCACC AAGGGCCGGG TAAAGCTGGT CATCCTGGTC ATCTGGGCCG TGGCCTTCTG    480
CAGCGCCGGG CCCATCTTCG TGCTGGTCGG AGTGGAGCAT GATAACGGCA CTGACCCTCG    540
GGACACCAAC GAGTGCCGCG CCACGGAGTT CGCCGTGCGC TCCGGGCTGC TTACCGTCAT    600
GGTCTGGGTG TCCAGTGTCT TCTTCTTCCT GCCTGTCTTC TGCCTCACTG TGCTCTATAG    660
CCTCATCGGC AGGAAGCTCT GGCGGAGGAA GCGCGGCGAG GCGGCGGTGG GCTCCTCGCT    720
CAGGGACCAG AACCACAAAC AAACCGTGAA AATGCTGGCT GTAGTGGTGT TTGCTTTCAT    780
ACTCTGCTGG CTGCCTTTCC ATGTAGGGCG ATATTTATTT TCCAAATCCT GGAGCCTGG    840
CTCTGTGGAG ATTGCTCAGA TCAGCCAATA CTGCAACCTC GTGTCCTTTG TCCTCTTCTA    900
CCTCAGTGCG GCCATCAACC CTATTCTGTA CAACATCATG TCCAAGAAGT ATCGGGTGGC    960
GGTGTTCAAA CTGCTGGGAT TTGAGCCCTT CTCACAGAGG AAACTCTCCA CTCTGAAGGA   1020
TGAAAGTTCT CGGGCCTGGA CAGAATCTAG TATTAATACA TGA                      1063
```

(2) INFORMATION FOR SEQ ID NO:2:

(i) SEQUENCE CHARACTERISTICS:
      (A) LENGTH: 302 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Met Leu Val Val Ser Arg Phe Arg Glu Met Arg Thr Thr Thr Asn Leu
 1               5                  10                  15

Tyr Leu Ser Ser Met Ala Phe Ser Asp Leu Leu Ile Phe Leu Cys Met
                20                  25                  30

Pro Leu Asp Leu Phe Arg Leu Trp Gln Tyr Arg Pro Trp Asn Leu Gly
            35                  40                  45

Asn Leu Leu Cys Lys Leu Phe Gln Phe Val Ser Glu Ser Cys Thr Tyr
```

```
                50                  55                  60
Ala Thr Val Leu Thr Ile Thr Ala Leu Ser Val Glu Arg Tyr Phe Ala
 65                  70                  75                  80

Ile Cys Phe Pro Leu Arg Ala Lys Val Val Thr Lys Gly Arg Val
                 85                  90                  95

Lys Leu Val Ile Leu Val Ile Trp Ala Val Ala Phe Cys Ser Ala Gly
                100                 105                 110

Pro Ile Phe Val Leu Val Gly Val Glu His Asp Asn Gly Thr Asp Pro
                115                 120                 125

Arg Asp Thr Asn Glu Cys Arg Ala Thr Glu Phe Ala Val Arg Ser Gly
130                 135                 140

Leu Leu Thr Val Met Val Trp Val Ser Ser Val Phe Phe Leu Pro
145                 150                 155                 160

Val Phe Cys Leu Thr Val Leu Tyr Ser Leu Ile Gly Arg Lys Leu Trp
                165                 170                 175

Arg Arg Lys Arg Gly Glu Ala Ala Val Gly Ser Ser Leu Arg Asp Gln
                180                 185                 190

Asn His Lys Gln Thr Val Lys Met Leu Ala Val Val Phe Ala Phe
    195                 200                 205

Ile Leu Cys Trp Leu Pro Phe His Val Gly Arg Tyr Leu Phe Ser Lys
210                 215                 220

Ser Leu Glu Pro Gly Ser Val Glu Ile Ala Gln Ile Ser Gln Tyr Cys
225                 230                 235                 240

Asn Leu Val Ser Phe Val Leu Phe Tyr Leu Ser Ala Ala Ile Asn Pro
                245                 250                 255

Ile Leu Tyr Asn Ile Met Ser Lys Lys Tyr Arg Val Ala Val Phe Lys
                260                 265                 270

Leu Leu Gly Phe Glu Pro Phe Ser Gln Arg Lys Leu Ser Thr Leu Lys
                275                 280                 285

Asp Glu Ser Ser Arg Ala Trp Thr Glu Ser Ser Ile Asn Thr
290                 295                 300

(2) INFORMATION FOR SEQ ID NO:3:

(i) SEQUENCE CHARACTERISTICS:
        (A) LENGTH: 353 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Leu Thr Leu Pro Asp Leu Gly Trp Asp Ala Pro Pro Glu Asn Asp Ser
  1               5                  10                  15

Leu Val Glu Glu Leu Leu Pro Leu Phe Pro Thr Pro Leu Leu Ala Gly
                 20                  25                  30

Val Thr Ala Thr Cys Val Ala Leu Phe Val Val Gly Ile Ala Gly Asn
                 35                  40                  45

Leu Leu Thr Met Leu Val Val Ser Arg Phe Arg Glu Met Arg Thr Thr
 50                  55                  60

Thr Asn Leu Tyr Leu Ser Ser Met Ala Phe Ser Asp Leu Leu Ile Phe
 65                  70                  75                  80

Leu Cys Met Pro Leu Asp Leu Phe Arg Leu Trp Gln Tyr Arg Pro Trp
                 85                  90                  95

Asn Leu Gly Asn Leu Leu Cys Lys Leu Phe Gln Phe Val Ser Glu Ser
```

```
              100                 105                 110
Cys Thr Tyr Ala Thr Val Leu Thr Ile Thr Ala Leu Ser Val Glu Arg
            115                 120                 125

Tyr Phe Ala Ile Cys Phe Pro Leu Arg Ala Lys Val Val Thr Lys
        130                 135                 140

Gly Arg Val Lys Leu Val Ile Leu Val Ile Trp Ala Val Ala Phe Cys
145                 150                 155                 160

Ser Ala Gly Pro Ile Phe Val Leu Val Gly Val Glu His Asp Asn Gly
                165                 170                 175

Thr Asp Pro Arg Asp Thr Asn Glu Cys Arg Ala Thr Glu Phe Ala Val
            180                 185                 190

Arg Ser Gly Leu Leu Thr Val Met Val Trp Val Ser Ser Val Phe Phe
        195                 200                 205

Phe Leu Pro Val Phe Cys Leu Thr Val Leu Tyr Ser Leu Ile Gly Arg
    210                 215                 220

Lys Leu Trp Arg Arg Lys Arg Gly Glu Ala Ala Val Gly Ser Ser Leu
225                 230                 235                 240

Arg Asp Gln Asn His Lys Gln Thr Val Lys Met Leu Ala Val Val Val
                245                 250                 255

Phe Ala Phe Ile Leu Cys Trp Leu Pro Phe His Val Gly Arg Tyr Leu
            260                 265                 270

Phe Ser Lys Ser Leu Glu Pro Gly Ser Val Glu Ile Ala Gln Ile Ser
        275                 280                 285

Gln Tyr Cys Asn Leu Val Ser Phe Val Leu Phe Tyr Leu Ser Ala Ala
    290                 295                 300

Ile Asn Pro Ile Leu Tyr Asn Ile Met Ser Lys Lys Tyr Arg Val Ala
305                 310                 315                 320

Val Phe Lys Leu Leu Gly Phe Glu Pro Phe Ser Gln Arg Lys Leu Ser
                325                 330                 335

Thr Leu Lys Asp Glu Ser Ser Arg Ala Trp Thr Glu Ser Ser Ile
            340                 345                 350

Asn Thr
```

(2) INFORMATION FOR SEQ ID NO:4:

(i) SEQUENCE CHARACTERISTICS:
        (A) LENGTH: 1029 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GCAGCCTCTC ACTTCCCTCT TTCCTCTCCT AGCATCCTCC CTGAGAGCCC GCGCTCGATA    60

CTCCTTTGCA CTCTTTCGCG CCTAAGAGAA CCTTCTCTGG GACCAGCCGG CTCCACCCTC   120

TCGGTCCTAT CCAAGAGCCA GTTAAGCAGA GCCCTAAGCA TGTGGAACGC GACCCCGAGC   180

GAGGAACCGG GGCCCAACCT CACGCTGCCA GACCTGGGCT GGGACGCTCC CCCTGAAAAC   240

GACTCGCTAG TGGAGGAGCT GCTGCCGCTC TTCCCCACGC CGCTGTTGGC GGGCGTCACC   300

GCCACCTGCG TGGCGCTCTT CGTGGTGGGT ATCGCGGGCA ACCTGCTCAC GATGCTGGTA   360

GTGTCACGCT TCCGCGAGAT GCGCACCACC ACCAACCTCT ACCTGTCCAG CATGGCCTTC   420

TCCGAACTAC TCATCTTCCT CTGCATGCCC CTCGAACTCT TCCGCCTTTG GCAGTACCGG   480

CCTTGGAACC TTGGCAACCT GCTCTGCAAA CTCTTCCAGT TCGTTAGCGA GAGCTGCACC   540
```

```
TACGCCACAG TGCTCACCAT CACCGCGCTG AGCGTCGAGC GCTACTTCGC CATCTGCTTC    600

CCGCTGCGGG CCAAGGTAGT GGTCACCAAG GGCCGGGTAA AGCTGGTCAT CCTGGTCATC    660

TGGGCCGTGG CCTTCTGCAG CGCCGGGCCC ATCTTCGTGC TGGTCGGAGT GGAGCATGAT    720

AACGGCACTG ACCCTCGGGA CACCAACGAG TGCCGCGCCA CGGAGTTCGC CGTGCGCTCC    780

GGGCTGCTTA CCGTCATGGT CTGGGTGTCC AGTGTCTTCT TCTTCCTGCC TGTCTTCTGC    840

CTCACTGTGC TCTATAGCCT CATCGGCAGG AAGCTCTGGC GGAGGAAGCG CGGCGAGGCG    900

GCGGTGGGCT CCTCGCTCAG GGACCAGAAC CACAAACAAA CCGTGAAAAT GCTGGGTGGG    960

TCTCAATGCG CCCTCGAGCT TTCTCTCCCG GGTCCCCTCC ACTCCTCGTG CCTTTTCTCT   1020

TCTCCCTGA                                                           1029
```

(2) INFORMATION FOR SEQ ID NO:5:

(i) SEQUENCE CHARACTERISTICS:
        (A) LENGTH: 289 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Trp Asn Ala Thr Pro Ser Glu Glu Pro Gly Pro Asn Leu Thr Leu
  1               5                  10                  15

Pro Asp Leu Gly Trp Asp Ala Pro Glu Asn Asp Ser Leu Val Glu
             20                  25                  30

Glu Leu Leu Pro Leu Phe Pro Thr Pro Leu Leu Ala Gly Val Thr Ala
         35                  40                  45

Thr Cys Val Ala Leu Phe Val Val Gly Ile Ala Gly Asn Leu Leu Thr
 50                  55                  60

Met Leu Val Val Ser Arg Phe Arg Glu Met Arg Thr Thr Thr Asn Leu
 65                  70                  75                  80

Tyr Leu Ser Ser Met Ala Phe Ser Glu Leu Leu Ile Phe Leu Cys Met
                 85                  90                  95

Pro Leu Glu Leu Phe Arg Leu Trp Gln Tyr Arg Pro Trp Asn Leu Gly
            100                 105                 110

Asn Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Thr Lys Gly Arg Val
145                 150                 155                 160

Lys Leu Val Ile Leu Val Ile Trp Ala Val Ala Phe Cys Ser Ala Gly
                165                 170                 175

Pro Ile Phe Val Leu Val Gly Val Glu His Asp Asn Gly Thr Asp Pro
            180                 185                 190

Arg Asp Thr Asn Glu Cys Arg Ala Thr Glu Phe Ala Val Arg Ser Gly
        195                 200                 205

Leu Leu Thr Val Met Val Trp Val Ser Ser Val Phe Phe Leu Pro
    210                 215                 220

Val Phe Cys Leu Thr Val Leu Tyr Ser Leu Ile Gly Arg Lys Leu Trp
225                 230                 235                 240

Arg Arg Lys Arg Gly Glu Ala Ala Val Gly Ser Ser Leu Arg Asp Gln
                245                 250                 255
```

```
Asn His Lys Gln Thr Val Lys Met Leu Gly Gly Ser Gln Cys Ala Leu
            260                 265                 270

Glu Leu Ser Leu Pro Gly Pro Leu His Ser Ser Cys Leu Phe Ser Ser
        275                 280                 285

Pro (2) INFORMATION FOR SEQ ID NO:6:

(i) SEQUENCE CHARACTERISTICS:
        (A) LENGTH: 1088 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CGCCCAGCGA AGAGCCGGGG TTCAACCTCA CACTGGCCGA CCTGGACTGG GATGCTTCCC    60

CCGGCAACGA CTCGCTGGGC GACGAGCTGC TGCAGCTCTT CCCCGCGCCG CTGCTGGCGG   120

GCGTCACAGC CACCTGCGTG GCACTCTTCG TGGTGGGTAT CGCTGGCAAC CTGCTCACCA   180

TGCTGGTGGT GTCGCGCTTC CGCGAGCTGC GCACCACCAC CAACCTCTAC CTGTCCAGCA   240

TGGCCTTCTC CGATCTGCTC ATCTTCCTCT GCATGCCCCT GGACCTCGTT CGCCTCTGGC   300

AGTACCGGCC CTGGAACTTC GGCGACCTCC TCTGCAAACT CTTCCAATTG GTCAGTGAGA   360

GCTGCACCTA CGCCACGGTG CTCACCATCA CAGCGCTGAG CGTCGAGCGC TACTTCGCCA   420

TCTGCTTCCC ACTCCGGGCC AAGGTGGTGG TCACCAAGGG GCGGGTGAAG CTGGTCATCT   480

TCGTCATCTG GGCCGTGGCC TTCTGCAGCG CCGGGCCCAT CTTCGTGCTA GTCGGGGTGG   540

AGCACGAGAA CGGCACCGAC CCTTGGGACA CCAACGAGTG CCGCCCCACC GAGTTTGCGG   600

TGCGCTCTGG ACTGCTCACG GTCATGGTGT GGGTGTCCAG CATCTTCTTC TTCCTTCCTG   660

TCTTCTGTCT CACGGTCCTC TACAGTCTCA TCGGCAGGAA GCTGTGGCGG AGGAGGCGCG   720

GCGATGCTGT CGTGGGTGCC TCGCTCAGGG ACCAGAACCA CAAGCAAACC GTGAAAATGC   780

TGGCTGTAGT GGTGTTTGCC TTCATCCTCT GCTGGCTCCC CTTCCACGTA GGGCGATATT   840

TATTTTCCAA ATCCTTTGAG CCTGGCTCCT TGGAGATTGC TCAGATCAGC CAGTACTGCA   900

ACCTCGTGTC CTTTGTCCTC TTCTACCTCA GTGCTGCCAT CAACCCCATT CTGTACAACA   960

TCATGTCCAA GAAGTACCGG GTGGCAGTGT TCAGACTTCT GGGATTCGAA CCCTTCTCCC  1020

AGAGAAAGCT CTCCACTCTG AAAGATGAAA GTTCTCGGGC CTGGACAGAA TCTAGTATTA  1080

ATACATGA                                                           1088

(2) INFORMATION FOR SEQ ID NO:7:

(i) SEQUENCE CHARACTERISTICS:
        (A) LENGTH: 302 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Met Leu Val Val Ser Arg Phe Arg Glu Leu Arg Thr Thr Thr Asn Leu
  1               5                  10                  15

Tyr Leu Ser Ser Met Ala Phe Ser Asp Leu Leu Ile Phe Leu Cys Met
             20                  25                  30
```

Pro Leu Asp Leu Val Arg Leu Trp Gln Tyr Arg Pro Trp Asn Phe Gly
         35                  40                  45

Asp Leu Leu Cys Lys Leu Phe Gln Phe Val Ser Glu Ser Cys Thr Tyr
     50                  55                  60

Ala Thr Val Leu Thr Ile Thr Ala Leu Ser Val Glu Arg Tyr Phe Ala
 65              70                  75                      80

Ile Cys Phe Pro Leu Arg Ala Lys Val Val Thr Lys Gly Arg Val
                 85                  90                  95

Lys Leu Val Ile Phe Val Ile Trp Ala Val Ala Phe Cys Ser Ala Gly
                100                 105                 110

Pro Ile Phe Val Leu Val Gly Val Glu His Glu Asn Gly Thr Asp Pro
             115                 120                 125

Trp Asp Thr Asn Glu Cys Arg Pro Thr Glu Phe Ala Val Arg Ser Gly
     130                 135                 140

Leu Leu Thr Val Met Val Trp Val Ser Ser Ile Phe Phe Phe Leu Pro
145                 150                 155                 160

Val Phe Cys Leu Thr Val Leu Tyr Ser Leu Ile Gly Arg Lys Leu Trp
                165                 170                 175

Arg Arg Arg Arg Gly Asp Ala Val Val Gly Ala Ser Leu Arg Asp Gln
                180                 185                 190

Asn His Lys Gln Thr Val Lys Met Leu Ala Val Val Phe Ala Phe
         195                 200                 205

Ile Leu Cys Trp Leu Pro Phe His Val Gly Arg Tyr Leu Phe Ser Lys
     210                 215                 220

Ser Phe Glu Pro Gly Ser Leu Glu Ile Ala Gln Ile Ser Gln Tyr Cys
225                 230                 235                 240

Asn Leu Val Ser Phe Val Leu Phe Tyr Leu Ser Ala Ala Ile Asn Pro
                245                 250                 255

Ile Leu Tyr Asn Ile Met Ser Lys Lys Tyr Arg Val Ala Val Phe Arg
                260                 265                 270

Leu Leu Gly Phe Glu Pro Phe Ser Gln Arg Lys Leu Ser Thr Leu Lys
             275                 280                 285

Asp Glu Ser Ser Arg Ala Trp Thr Glu Ser Ser Ile Asn Thr
         290                 295                 300

(2) INFORMATION FOR SEQ ID NO:8:

(i) SEQUENCE CHARACTERISTICS:
        (A) LENGTH: 361 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Pro Ser Glu Glu Pro Gly Phe Asn Leu Thr Leu Ala Asp Leu Asp Trp
 1               5                  10                  15

Asp Ala Ser Pro Gly Asn Asp Ser Leu Gly Asp Glu Leu Leu Gln Leu
             20                  25                  30

Phe Pro Ala Pro Leu Leu Ala Gly Val Thr Ala Thr Cys Val Ala Leu
         35                  40                  45

Phe Val Val Gly Ile Ala Gly Asn Leu Leu Thr Met Leu Val Val Ser
     50                  55                  60

Arg Phe Arg Glu Leu Arg Thr Thr Thr Asn Leu Tyr Leu Ser Ser Met
 65                  70                  75                  80

```
Ala Phe Ser Asp Leu Leu Ile Phe Leu Cys Met Pro Leu Asp Leu Val
                85                  90                  95
Arg Leu Trp Gln Tyr Arg Pro Trp Asn Phe Gly Asp Leu Leu Cys Lys
            100                 105                 110
Leu Phe Gln Phe Val Ser Glu Ser Cys Thr Tyr Ala Thr Val Leu Thr
        115                 120                 125
Ile Thr Ala Leu Ser Val Glu Arg Tyr Phe Ala Ile Cys Phe Pro Leu
130                 135                 140
Arg Ala Lys Val Val Val Thr Lys Gly Arg Val Lys Leu Val Ile Phe
145                 150                 155                 160
Val Ile Trp Ala Val Ala Phe Cys Ser Ala Gly Pro Ile Phe Val Leu
                165                 170                 175
Val Gly Val Glu His Glu Asn Gly Thr Asp Pro Trp Asp Thr Asn Glu
                180                 185                 190
Cys Arg Pro Thr Glu Phe Ala Val Arg Ser Gly Leu Leu Thr Val Met
            195                 200                 205
Val Trp Val Ser Ser Ile Phe Phe Phe Leu Pro Val Phe Cys Leu Thr
        210                 215                 220
Val Leu Tyr Ser Leu Ile Gly Arg Lys Leu Trp Arg Arg Arg Arg Gly
225                 230                 235                 240
Asp Ala Val Val Gly Ala Ser Leu Arg Asp Gln Asn His Lys Gln Thr
                245                 250                 255
Val Lys Met Leu Ala Val Val Val Phe Ala Phe Ile Leu Cys Trp Leu
                260                 265                 270
Pro Phe His Val Gly Arg Tyr Leu Phe Ser Lys Ser Phe Glu Pro Gly
            275                 280                 285
Ser Leu Glu Ile Ala Gln Ile Ser Gln Tyr Cys Asn Leu Val Ser Phe
        290                 295                 300
Val Leu Phe Tyr Leu Ser Ala Ala Ile Asn Pro Ile Leu Tyr Asn Ile
305                 310                 315                 320
Met Ser Lys Lys Tyr Arg Val Ala Val Phe Arg Leu Leu Gly Phe Glu
                325                 330                 335
Pro Phe Ser Gln Arg Lys Leu Ser Thr Leu Lys Asp Glu Ser Ser Arg
                340                 345                 350
Ala Trp Thr Glu Ser Ser Ile Asn Thr
            355                 360

(2) INFORMATION FOR SEQ ID NO:9:

(i) SEQUENCE CHARACTERISTICS:
        (A) LENGTH: 1122 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCGCCTCACG CTCCCGCTTC GCGGCGCCTG GTCCCTGCGG TCCCCACTCG CTGCGACGCT      60

TTGGGAAGTG CGAGATGGAA CTGGATCGAG AACGCAAATG CGAGGCAGGG CTGGTGACAG     120

CATCCTCCCT ACGCGTCTGC ACCCGCTCCT CCCTCGCACC CTCCCGCGCC TAAGCGGACC     180

TCCTCGGGAG CCAGCTCGGT CCAGCCTCCC AGCGCAGTCA CGTCCCAGAG CCTGTTCAGC     240

TGAGCCGGCA GCATGTGGAA CGCGACGCCC AGCGAAGAGC CGGGGTTCAA CCTCACACTG     300

GCCGACCTGG ACTGGGATGC TTCCCCCGGC AACGACTCGC TGGGCGACGA GCTGCTGCAG     360
```

```
CTCTTCCCCG CGCCGCTGCT GGCGGGCGTC ACAGCCACCT GCGTGGCACT CTTCGTGGTG      420

GGTATCGCTG GCAACCTGCT CACCATGCTG GTGGTGTCGC GCTTCCGCGA GCTGCGCACC      480

ACCACCAACC TCTACCTGTC CAGCATGGCC TTCTCCGATC TGCTCATCTT CCTCTGCATG      540

CCCCTGGACC TCGTTCGCCT CTGGCAGTAC CGGCCCTGGA ACTTCGGCGA CCTCCTCTGC      600

AAACTCTTCC AATTCGTCAG TGAGAGCTGC ACCTACGCCA CGGTGCTCAC CATCACAGCG      660

CTGAGCGTCG AGCGCTACTT CGCCATCTGC TTCCCACTCC GGGCCAAGGT GGTGGTCACC      720

AAGGGGCGGG TGAAGCTGGT CATCTTCGTC ATCTGGGCCG TGGCCTTCTG CAGCGCCGGG      780

CCCATCTTCG TGCTAGTCGG GGTGGAGCAC GAGAACGGCA CCGACCCTTG GGACACCAAC      840

GAGTGCCGCC CCACCGAGTT TGCGGTGCGC TCTGGACTGC TCACGGTCAT GGTGTGGGTG      900

TCCAGCATCT TCTTCTTCCT TCCTGTCTTC TGTCTCACGG TCCTCTACAG TCTCATCGGC      960

AGGAAGCTGT GGCGGAGGAG GCGCGGCGAT GCTGTCGTGG GTGCCTCGCT CAGGGACCAG     1020

AACCACAAGC AAACCGTGAA AATGCTGGGT GGGTCTCAGC GCGCGCTCAG GCTTTCTCTC     1080

GCGGGTCCTA TCCTCTCCCT GTGCCTTCTC CCTTCTCTCT GA                        1122
```

(2) INFORMATION FOR SEQ ID NO:10:

(i) SEQUENCE CHARACTERISTICS:
        (A) LENGTH: 289 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Trp Asn Ala Thr Pro Ser Glu Glu Pro Gly Phe Asn Leu Thr Leu
 1               5                  10                  15

Ala Asp Leu Asp Trp Asp Ala Ser Pro Gly Asn Asp Ser Leu Gly Asp
             20                  25                  30

Glu Leu Leu Gln Leu Phe Pro Ala Pro Leu Leu Ala Gly Val Thr Ala
         35                  40                  45

Thr Cys Val Ala Leu Phe Val Val Gly Ile Ala Gly Asn Leu Leu Thr
     50                  55                  60

Met Leu Val Val Ser Arg Phe Arg Glu Leu Arg Thr Thr Thr Asn Leu
 65                  70                  75                  80

Tyr Leu Ser Ser Met Ala Phe Ser Asp Leu Leu Ile Phe Leu Cys Met
                 85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
        195                 200                 205

Leu Leu Thr Val Met Val Trp Val Ser Ser Ile Phe Phe Phe Leu Pro
```

-continued

```
            210                 215                 220
Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Gly Gly Ser Gln Arg Ala Leu
                260                 265                 270

Arg Leu Ser Leu Ala Gly Pro Ile Leu Ser Leu Cys Leu Leu Pro Ser
            275                 280                 285

Leu
```

(2) INFORMATION FOR SEQ ID NO:11:

(i) SEQUENCE CHARACTERISTICS:
        (A) LENGTH: 836 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
ATCTGCTCAT CTTCCTCTGC ATGCCCCTGG ACCTCGTTCG CCTCTGGCAG TACCGGCCCT    60
GGAACTTCGG CGACCTCCTC TGCAAACTCT TCCAATTCGT CAGTGAGAGC TGCACCTACG   120
CCACGGTGCT CACCATCACA GCGCTGAGCG TCGAGCGCTA CTTCGCCATC TGCTTCCCAC   180
TCCGGGCCAA GGTGGTGGTC ACCAAGGGGC GGGTGAAGCT GGTCATCTTC GTCATCTGGG   240
CCGTGGCCTT CTGCAGCGCC GGGCCCATCT TCGTGCTAGT CGGGGTGGAG CACGAGAACG   300
GCACCGACCC TTGGGACACC AACGAGTGCC GCCCCACCGA GTTTGCGGTG CGCTCTGGAC   360
TGCTCACGGT CATGGTGTGG GTGTCCAGCA TCTTCTTCTT CCTTCCTGTC TTCTGTCTCA   420
CGGTCCTCTA CAGTCTCATC GGCAGGAAGC TGTGGCGGAG GAGGCGCGGC GATGCTGTCG   480
TGGGTGCCTC GCTCAGGGAC CAGAACCACA AGCAAACCGT GAAAATGCTG GCTGTAGTGG   540
TGTTTGCCTT CATCCTCTGC TGGCTCCCCT TCCACGTAGG GCGATATTTA TTTTCCAAAT   600
CCTTTGAGCC TGGCTCCTTG GAGATTGCTC AGATCAGCCA GTACTGCAAC CTCGTGTCCT   660
TTGTCCTCTT CTACCTCAGT GCTGCCATCA ACCCCATTCT GTACAACATC ATGTCCAAGA   720
AGTACCGGGT GGCAGTGTTC AGACTTCTGG GATTCGAACC CTTCTCCCAG AGAAAGCTCT   780
CCACTCTGAA AGATGAAAGT TCTCGGGCCT GGACAGAATC TAGTATTAAT ACATGA       836
```

(2) INFORMATION FOR SEQ ID NO:12:

(i) SEQUENCE CHARACTERISTICS:
        (A) LENGTH: 271 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Pro Leu Asp Leu Val Arg Leu Trp Gln Tyr Arg Pro Trp Asn Phe
1               5                   10                  15

Gly Asp Leu Leu Cys Lys Leu Phe Gln Phe Val Ser Glu Ser Cys Thr
                20                  25                  30

Tyr Ala Thr Val Leu Thr Ile Thr Ala Leu Ser Val Glu Arg Tyr Phe
            35                  40                  45
```

```
Ala Ile Cys Phe Pro Leu Arg Ala Lys Val Val Thr Lys Gly Arg
    50                  55                  60

Val Lys Leu Val Ile Phe Val Ile Trp Ala Val Ala Phe Cys Ser Ala
65                  70                  75                  80

Gly Pro Ile Phe Val Leu Gly Val Glu His Glu Asn Gly Thr Asp
                85                  90                  95

Pro Trp Asp Thr Asn Glu Cys Arg Pro Thr Glu Phe Ala Val Arg Ser
                100                 105                 110

Gly Leu Leu Thr Val Met Val Trp Val Ser Ser Ile Phe Phe Leu
            115                 120                 125

Pro Val Phe Cys Leu Thr Val Leu Tyr Ser Leu Ile Gly Arg Lys Leu
            130                 135                 140

Trp Arg Arg Arg Arg Gly Asp Ala Val Val Gly Ala Ser Leu Arg Asp
145                 150                 155                 160

Gln Asn His Lys Gln Thr Val Lys Met Leu Ala Val Val Phe Ala
                165                 170                 175

Phe Ile Leu Cys Trp Leu Pro Phe His Val Gly Arg Tyr Leu Phe Ser
                180                 185                 190

Lys Ser Phe Glu Pro Gly Ser Leu Glu Ile Ala Gln Ile Ser Gln Tyr
            195                 200                 205

Cys Asn Leu Val Ser Phe Val Leu Phe Tyr Leu Ser Ala Ala Ile Asn
    210                 215                 220

Pro Ile Leu Tyr Asn Ile Met Ser Lys Lys Tyr Arg Val Ala Val Phe
225                 230                 235                 240

Arg Leu Leu Gly Phe Glu Pro Phe Ser Gln Arg Lys Leu Ser Thr Leu
                245                 250                 255

Lys Asp Glu Ser Ser Arg Ala Trp Thr Glu Ser Ser Ile Asn Thr
                260                 265                 270

(2) INFORMATION FOR SEQ ID NO:13:

(i) SEQUENCE CHARACTERISTICS:
        (A) LENGTH: 366 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
                20                  25                  30

Glu Leu Leu Gln Leu Phe Pro Ala Pro Leu Leu Ala Gly Val Thr Ala
            35                  40                  45

Thr Cys Val Ala Leu Phe Val Val Gly Ile Ala Gly Asn Leu Leu Thr
    50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
                100                 105                 110

Asp Leu Leu Cys Lys Leu Phe Gln Phe Val Ser Glu Ser Cys Thr Tyr
            115                 120                 125
```

```
Ala Thr Val Leu Thr Ile Thr Ala Leu Ser Val Glu Arg Tyr Phe Ala
        130                 135                 140

Ile Cys Phe Pro Leu Arg Ala Lys Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
                180                 185                 190

Trp Asp Thr Asn Glu Cys Arg Pro Thr Glu Phe Ala Val Arg Ser Gly
        195                 200                 205

Leu Leu Thr Val Met Val Trp Val Ser Ser Ile Phe Phe Leu Pro
210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Ala Val Val Phe Ala Phe
        260                 265                 270

Ile Leu Cys Trp Leu Pro Phe His Val Gly Arg Tyr Leu Phe Ser Lys
275                 280                 285

Ser Phe Glu Pro Gly Ser Leu Glu Ile Ala Gln Ile Ser Gln Tyr Cys
        290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Arg
                325                 330                 335

Leu Leu Gly Phe Glu Pro Phe Ser Gln Arg Lys Leu Ser Thr Leu Lys
                340                 345                 350

Asp Glu Ser Ser Arg Ala Trp Thr Glu Ser Ser Ile Asn Thr
        355                 360                 365

(2) INFORMATION FOR SEQ ID NO:14:

(i) SEQUENCE CHARACTERISTICS:
        (A) LENGTH: 3129 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

ATGTGGAACG CGACCCCCAG CGAGGAGCCG GAGCCTAACG TCACGTTGGA CCTGGATTGG      60

GACGCTTCCC CCGGCAACGA CTCACTGCCT GACGAACTGC TGCCGCTGTT CCCCGCTCCG     120

CTGCTGGCAG GCGTCACCGC CACCTGCGTG GCGCTCTTCG TGGTGGGCAT CTCAGGCAAC     180

CTGCTCACTA TGCTGGTGGT GTCCCGCTTC CGCGAGCTGC GCACCACCAC CAACCTCTAC     240

CTGTCCAGCA TGGCCTTCTC GGATCTGCTC ATCTTCCTGT GCATGCCGCT GGACCTCGTC     300

CGCCTCTGGC AGTACCGGCC CTGGAACTTC GGCGACCTGC TCTGCAAACT CTTCCAGTTT     360

GTCAGCGAGA GCTGCACCTA CGCCACGGTC CTCACCATCA CCGCGCTGAG CGTCGAGCGC     420

TACTTCGCCA TCTGCTTCCC TCTGCGGGCC AAGGTGGTGG TCACTAAGGG CCGCGTGAAG     480

CTGGTCATCC TTGTCATCTG GGCCGTGGCT TTCTGCAGCG CGGGGCCCAT CTTCGTGCTG     540

GTGGGCGTGG AGCACGAAAA CGGCACAGAT CCCCGGGACA CCAACGAATG CCGCGCCACC     600

GAGTTCGCTG TGCGCTCTGG GCTGCTCACC GTCATGGTGT GGGTGTCCAG CGTCTTCTTC     660
```

```
TTTCTACCGG TCTTCTGCCT CACTGTGCTC TACAGTCTCA TCGGGAGGAA GCTATGGCGG    720

AGACGCGGAG ATGCAGCGGT GGGCGCCTCG CTCCGGGACC AGAACCACAA GCAGACAGTG    780

AAGATGCTTG GTGAGTCCTG GCACCCGCTG ACCTTTCTTC CCCCACTGCC TGCCCTTCCC    840

CAGCGGCCTC TATTTCTGTT TCTCATCATC TCCGCTCCCC AAGTCTCTCA AGTCTCTGTC    900

TTTCTCTGCC TCTCTCACCT TGGTTCTCGG TCTCACTGCT TTCTGTTTTC TTCCTGTCTT    960

TTCCTGTATC TTGTCCACGA AAAAGAACCC TCATATTGGT AATTCCTTAA AACGAGGAAC   1020

CTTGGTCTGG GAAAATTGGT CCAAGATGGA AATACCTCAC GGTTTATTGA GCCCCTAATT   1080

GTTAACGGTT TAGCTTCTTG TCTCACATAG AATTTGTGGT TATCAAAGTA ATAATATTAA   1140

GGTAAGCAGG CAGGTAATGG GTTTAGAAAT CACTCCATGG TAAGTCTAAC CACAAATTTG   1200

GGTCACTCTG TTAAGGACGG CTTATAGATG TATTTTGTTT GTTTTCAATA TTGGGATTTG   1260

TTTTCTGCCC TGCATCTTTC TCAGATAATT ACATCCACTC TGTTTAGTCT ATGGTTTTGC   1320

CAGGAGGGGC TTCATGCTGG GGTCTCCTTT TTCTTGTTTT TGTATTTGTC TCCCCAGTAA   1380

TATAGGCCAG GATAGGGTGG AGAAGTCATC CTTTCCTCAA ACTGTCCTTC AGGAAGGTCT   1440

GGGTACTGAA CGGTTACTGC ATAAACTCTG CTTCCCCAAA GGCATGTGCT TGGTGTGGTA   1500

AAGTCATGAA GATGGTGCTC ATGTCCAAGA GGAACCTCTG ATCTCACTTT TCAAGGGATT   1560

TCATGTTTGC TGACATTTAA TACTTGTTAG TTTTTGCAGG GGGATGATTT CTCATTTGCA   1620

ATTTTATTAT TCTCAAATTC TGCATGTCAG AATGTTAGAG ATTTCTCAGG GATGTCAGGT   1680

TCTGTTTCCA GATGAGTGAT TGCCCTGTGT CCTCCATTGG ACTGTAAACT CATATGCACC   1740

AGACAGGGTC TACATTGCTG CCGTGGTGCA TAGCCTTCCA TGTGTCACTT AGTCCTAAAG   1800

AGAAGTTACT AATAACCTAA TCTCACTAAT CTCACTGGCA TCTCAATGCC GATCCCATTG   1860

TCATCTGAAA ATTTGAAGGG ACATTAAAG TGGCACAGGG ACCAGAACAA TATTTTTCTC   1920

TCATTGCTGA ATTTTAAAAA CAATCTAAAA AATTGGAATT CTTGAAGAAA CTATCTTATA   1980

TGACTAAAAT GAAGCCTTGG GTGGGTGCTA ATTATTATTG TCTGGCTTAC CTGCCCCCCC   2040

CACTACTTAT ATCTTTTAGA GATGACACAG ACTTGCTTTC CCTGTGGCTA CTAATCCCAA   2100

TTGCACATTC AGTCCCTTGA TAGACTTACT CTAAAAATCT AAGTTCAGCG GTCCACGAAA   2160

CATAACAAAG CCTGTCCTAA AACAGAAAGA AAGAAAGAAA GAAAGAAAGA AAGAAAGAAA   2220

GAAAGAAAGA AAGAAAGAAA ACAGAAGACA AACAAGGTCT TTCCCCATTC CCTAACATAC   2280

AGGAATGGAA ATTATTAAGT CTACGTGATA GCCAATGAAT CTGTTTCTTA AGTATGCCCA   2340

CAAGGGTGCT GCCGGAGCCA TTGCTCAGGG CTGGAGTATT TACTGGGCAT GCTTGACCCC   2400

AGCATGGAGG GTGAGAAGTG CTCCTGGGAA CTCTGATCCA CTGCTGTGGT GGAGAGCAAA   2460

CACCTGGCCT CATTTATACT TGTTGTCTGT ATAATGCATA TAAATGGGGG ATAATCATTA   2520

CTAAACTGTT TAGCTGAGCC TCATGTCAGT CAATCACAAA GCAGAGTAAT TACCACACAG   2580

ACTGGGAAGC TCAGTGAAGA TTGTTAGCGG TTGGTCTGAC AGTCTTGCTG TGTGCTATAG   2640

TGTTAGACCC AACGGAGGCA GTATTTATAA GGAGGGCAGG GTTCCATGTT TCCCGTGTTA   2700

AAGAGCAAGA GATGATGTTT GTCAGTAGGC ATGCAGCTCA TGGTGAAAAG AAAGTCCAGA   2760

CTTAAAGATG TGAAGTGATT TGTGCTTTGC CCCACCCTGA CAGTCTCTCT CTGTGTGCCT   2820

TCAGCTGTGG TGGTGTTTGC TTTCATCCTC TGCTGGCTGC CCTTCCACGT GGGAAGATAC   2880

CTCTTTTCCA AGTCCTTCGA GCCTGGCTCT CTGGAGATCG CTCAGATCAG CCAGTACTGC   2940

AACCTGGTGT CCTTTGTCCT CTTCTACCTC AGCGCTGCCA TCAACCCCAT TCTGTACAAC   3000
```

```
ATCATGTCCA AGAAGTACCG GGTGGCAGTG TTCAAACTGC TAGGATTTGA ATCCTTCTCC    3060

CAGAGAAAGC TTTCCACTCT GAAGGATGAG AGTTCCCGGG CCTGGACAAA GTCGAGCATC    3120

AACACATGA                                                            3129
```

(2) INFORMATION FOR SEQ ID NO:15:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
ATGTGGAACG CGACCCCCAG CGAGGAGCCG GAGCCTAACG TCACGTTGGA CCTGGATTGG      60

GACGCTTCCC CCGGCAACGA CTCACTGCCT GACGAACTGC TGCCGCTGTT CCCCGCTCCG     120

CTGCTGGCAG GCGTCACCGC CACCTGCGTG GCGCTCTTCG TGGTGGGCAT CTCAGGCAAC     180

CTGCTCACTA TGCTGGTGGT GTCCCGCTTC CGCGAGCTGC GCACCACCAC CAACCTCTAC     240

CTGTCCAGCA TGGCCTTCTC GGATCTGCTC ATCTTCCTGT GCATGCCGCT GGACCTCGTC     300

CGCCTCTGGC AGTACCGGCC CTGGAACTTC GGCGACCTGC TCTGCAAACT CTTCCAGTTT     360

GTCAGCGAGA GCTGCACCTA CGCCACGGTC CTCACCATCA CCGCGCTGAG CGTCGAGCGC     420

TACTTCGCCA TCTGCTTCCC TCTGCGGGCC AAGGTGGTGG TCACTAAGGG CCGCGTGAAG     480

CTGGTCATCC TTGTCATCTG GGCCGTGGCT TTCTGCAGCG CGGGGCCCAT CTTCGTGCTG     540

GTGGGCGTGG AGCACGAAAA CGGCACAGAT CCCCGGGACA CCAACGAATG CCGCGCCACC     600

GAGTTCGCTG TGCGCTCTGG GCTGCTCACC GTCATGGTGT GGGTGTCCAG CGTCTTCTTC     660

TTTCTACCGG TCTTCTGCCT CACTGTGCTC TACAGTCTCA TCGGGAGGAA GCTATGGCGG     720

AGACGCGGAG ATGCAGCGGT GGGCGCCTCG CTCCGGGACC AGAACCACAA GCAGACAGTG     780

AAGATGCTTG CTGTGGTGGT GTTTGCTTTC ATCCTCTGCT GGCTGCCCTT CCACGTGGGA     840

AGATACCTCT TTTCCAAGTC CTTCGAGCCT GGCTCTCTGG AGATCGCTCA GATCAGCCAG     900

TACTGCAACC TGGTGTCCTT TGTCCTCTTC TACCTCAGCG CTGCCATCAA CCCCATTCTG     960

TACAACATCA TGTCCAAGAA GTACCGGGTG GCAGTGTTCA AACTGCTAGG ATTTGAATCC    1020

TTCTCCCAGA GAAAGCTTTC CACTCTGAAG GATGAGAGTT CCCGGGCCTG GACAAAGTCG    1080

AGCATCAACA CA                                                       1092
```

(2) INFORMATION FOR SEQ ID NO:16:

(i) SEQUENCE CHARACTERISTICS:
        (A) LENGTH: 364 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Met Trp Asn Ala Thr Pro Ser Glu Glu Pro Glu Pro Asn Val Thr Leu
  1               5                  10                  15

Asp Leu Asp Trp Asp Ala Ser Pro Gly Asn Asp Ser Leu Pro Asp Glu
             20                  25                  30

Leu Leu Pro Leu Phe Pro Ala Pro Leu Leu Ala Gly Val Thr Ala Thr
         35                  40                  45
```

-continued

```
Cys Val Ala Leu Phe Val Val Gly Ile Ser Gly Asn Leu Leu Thr Met
    50                  55                  60

Leu Val Val Ser Arg Phe Arg Glu Leu Arg Thr Thr Thr Asn Leu Tyr
65                  70                  75                  80

Leu Ser Ser Met Ala Phe Ser Asp Leu Leu Ile Phe Leu Cys Met Pro
                85                  90                  95

Leu Asp Leu Val Arg Leu Trp Gln Tyr Arg Pro Trp Asn Phe Gly Asp
                100                 105                 110

Leu Leu Cys Lys Leu Phe Gln Phe Val Ser Glu Ser Cys Thr Tyr Ala
            115                 120                 125

Thr Val Leu Thr Ile Thr Ala Leu Ser Val Glu Arg Tyr Phe Ala Ile
        130                 135                 140

Cys Phe Pro Leu Arg Ala Lys Val Val Val Thr Lys Gly Arg Val Lys
145                 150                 155                 160

Leu Val Ile Leu Val Ile Trp Ala Val Ala Phe Cys Ser Ala Gly Pro
                165                 170                 175

Ile Phe Val Leu Val Gly Val Glu His Glu Asn Gly Thr Asp Pro Arg
                180                 185                 190

Asp Thr Asn Glu Cys Arg Ala Thr Glu Phe Ala Val Arg Ser Gly Leu
            195                 200                 205

Leu Thr Val Met Val Trp Val Ser Ser Val Phe Phe Phe Leu Pro Val
    210                 215                 220

Phe Cys Leu Thr Val Leu Tyr Ser Leu Ile Gly Arg Lys Leu Trp Arg
225                 230                 235                 240

Arg Arg Gly Asp Ala Ala Val Gly Ala Ser Leu Arg Asp Gln Asn His
                245                 250                 255

Lys Gln Thr Val Lys Met Leu Ala Val Val Phe Ala Phe Ile Leu
            260                 265                 270

Cys Trp Leu Pro Phe His Val Gly Arg Tyr Leu Phe Ser Lys Ser Phe
        275                 280                 285

Glu Pro Gly Ser Leu Glu Ile Ala Gln Ile Ser Gln Tyr Cys Asn Leu
    290                 295                 300

Val Ser Phe Val Leu Phe Tyr Leu Ser Ala Ala Ile Asn Pro Ile Leu
305                 310                 315                 320

Tyr Asn Ile Met Ser Lys Lys Tyr Arg Val Ala Val Phe Lys Leu Leu
                325                 330                 335

Gly Phe Glu Ser Phe Ser Gln Arg Lys Leu Ser Thr Leu Lys Asp Glu
                340                 345                 350

Ser Ser Arg Ala Trp Thr Lys Ser Ser Ile Asn Thr
            355                 360
```

GROWTH HORMONE SECRETAGOGUE RECEPTOR FAMILY

The instant application claims priority under 35 U.S.C. §119(e) to U.S. provisional application serial Nos. 60/008,582 and 60/018,962, filed Dec. 13, 1995 and Jun. 6, 1996, respectively.

FIELD OF THE INVENTION

This invention relates to a new family of receptors, which includes the growth hormone secretagogue receptors (GHSRs) and growth hormone secretagogue-related receptors (GHSRRs), nucleic acids encoding these receptors; and to the use of a GHSR to identify growth hormone secretagogues and compounds that modulate GHSR function.

BACKGROUND OF THE INVENTION

Growth hormone (GH) is an anabolic hormone capable of promoting linear growth, weight gain and whole body nitrogen retention. Classically, GH is thought to be released primarily from the somatotroph cells of the anterior pituitary under the coordinate regulation of two hypothalamic hormones, growth hormone releasing factor (GHRF or GRF) and somatostatin. Both GHRF stimulation and somatostatin inhibition of the release of GH occurs by the specific engagement of receptors on the cell membrane of the somatotroph.

Recent evidence has been mounting which suggests that GH release is also stimulated by a group of short peptides, the growth hormone releasing peptides (GHRP; GHRP-6, GHRP-2 [hexarelin]) which are described, for example, in U.S. Pat. No. 4,411,890, PCT Patent Pub. No. WO 89/07110, PCT Patent Pub. No. WO 89/071 11, PCT Patent Pub. No. WO 93/04081, and *J. Endocrinol Invest.*, 15 (Suppl 4), 45 (1992). These peptides function by selectively binding to distinct somatotroph cell membrane receptor, the growth hormone secretagogue receptor(s) (GHSRs). A medicinal chemical approach has resulted in the design of several classes of orally-active, low molecular weight, non-peptidyl compounds which bind specifically to this receptor and result in the pulsatile release of GH. Such compounds possessing growth hormone secretagogue activity are disclosed, for example, in the following: U.S. Pat. Nos. 3,239,345; 4,036,979; 4,411,890; 5,206,235; 5,283,241; 5,284,841; 5,310,737; 5,317,017; 5,374,721; 5,430,144; 5,434,261; 5,438,136; 5,494,919; 5,494,920; 5,492,916; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95114666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/3431 1; PCT Patent Pub. No. WO 96/02530; *Science*, 260, 1640–1643 (Jun. 11, 1993); *Ann. Rep. Med. Chem.*, 28, 177–186 (1993); *Bioorg. Med. Chem. Ltrs.*, 4(22), 2709–2714 (1994); and *Proc. Natl. Acad. Sci. USA* 92, 7001–7005 (July 1995).

The use of orally-active agents which stimulate the pulsatile release of GH would be a significant advance in the treatment of growth hormone deficiency in children and adults as well as provide substantial benefit under circumstances where the anabolic effects of GH might be exploited clinically (e.g. post-hip fracture rehabilitation, the frail elderly and in post-operative recovery patients).

It would also be desirable to know the molecular structure of growth hormone secretagogue receptors in order to analyze this new receptor family and understand its normal physiological role in concert with the actions of GHRF and somatostatin. This could lead to a better understanding of the in vivo processes which occur upon ligand-receptor binding. Further, it would be desirable to use cloned-growth hormone secretagogue receptors as essential components of an assay system which can identify new growth hormone secretagogues.

DETAILED DESCRIPTION OF THE INVENTION

This invention relates to a novel family of receptors which includes growth hormone secretagogue receptors (GHSRs) and growth hormone secretagogue-related receptors (GHSRRs).

A first aspect of this invention are the growth hormone secretagogue receptors, which are free from receptor associated proteins. GHSRs may be from any species, and in further embodiments may be isolated or purified. One embodiment of this invention is human growth hormone secretagogue receptor (hGHSR), free from receptor-associated proteins. A further aspect of this invention is hGHSR which is isolated or purified.

Another aspect of this invention is swine growth hormone secretagogue receptor (sGHSR), free from receptor-associated proteins. A further aspect of this invention is sGHSR which is isolated or purified.

Another aspect of this invention is rat growth hormone secretagogue receptor (rGHSR), free from receptor-associated proteins. A further aspect of this invention is sGHSR which is isolated or purified.

Another aspect of this invention are human, swine and rat GHSRs which are encoded by substantially the same nucleic acid sequences, but which have undergone changes in splicing or other RNA processing-derived modifications or mutagenesis induced changes, so that the expressed protein has a homologous, but different amino acid sequence from the native forms. These variant forms may have different and/or additional functions in human and animal physiology or in vitro in cell based assays.

Another aspect of this invention are the growth hormone secretagogue-related receptors, free from associated receptor proteins. A further embodiment are GHSRRs which are isolated or purified. These may be from any species, including human, mouse, rat and swine.

Growth hormone secretagogue receptors are proteins containing various functional domains, including one or more domains which anchor the receptor in the cell membrane, and at least one ligand binding domain. As with many receptor proteins, it is possible to modify many of the amino acids, particularly those which are not found in the ligand binding domain, and still retain at least a percentage of the biological activity of the original receptor. In accordance with this invention, it has been shown that the N-terminal portions of the GHSR are not essential for its activation by the Growth Hormone Secretagogues (GHSs). Thus this invention specifically includes modified functionally equivalent GHSRs which have deleted, truncated, or mutated N-terminal portions. This invention also specifically includes modified functionally equivalent GHSRs which contain modified and/or deletions in other domains, which are not accompanied by a loss of functional activity.

Additionally, it is possible to modify other functional domains such as those that interact with second messenger effector systems, by altering binding specificity and/or selectivity. Such functionally equivalent mutant receptors are also within the scope of this invention.

A further aspect of this invention are nucleic acids which encode a growth hormone secretagogue receptor or a functional equivalent from swine, human, rat or other species. These nucleic acids may be free from associated nucleic acids, or they may be isolated or purified. For most cloning purposes, cDNA is a preferred nucleic acid, but this invention specifically includes other forms of DNA as well as RNAs which encode a GHSR or a functional equivalent.

Yet another aspect of this invention relates to vectors which comprise nucleic acids encoding a GHSR or a functional equivalent. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA that can encode a GHSR. It is well within the skill of the ordinary artisan to determine an appropriate vector for a particular gene transfer or other use.

A further aspect of this invention are host cells which are transformed with a gene which encodes a growth hormone secretagogue receptor or a functional equivalent. The host cell may or may not naturally express a GHSR on the cell membrane. Preferably, once transformed, the host cells are able to express the growth hormone secretagogue receptor or a functional equivalent on the cell membrane. Depending on the host cell, it may be desirable to adapt the DNA so that particular codons are used in order to optimize expression. Such adaptations are known in the art, and these nucleic acids are also included within the scope of this invention. Generally, mammalian cell lines, such as COS, HEK-293, CHO, HeLa, NS/O, CV-1, GC, GH3 or VERO cells are preferred host cells, but other cells and cell lines such as Xenopus oocytes or insect cells, may also be used.

Growth hormone secretagogue related receptors are related to GHRS, but are encoded by a distinct gene. The GHRR genes may be identified by hybridization (using relaxed or moderate stringency post-hybridizational washing conditions) of cDNA of GHR DNA to genonic DNA. These sequences have a high degree of similarity to GHR.

Another aspect of this invention is a process for identifying nucleic acids encoding growth hormone secretagogue related receptors comprising hybridizing a first nucleic acid encoding a growth hormone secretagogue receptor with a second nucleic acid suspected of comprising nucleic acids encoding a growth hormone secretagogue, wherein the hybridizing takes place under relaxed or moderate post hybridizational washing conditions; and identify areas of the second nucleic acid where hybridization occurred.

BRIEF DESCRIPTION OF THE DRAWINGS

FIG. 1 is the DNA of Swine GHSR (type I) contained in Clone 7-3 (SEQ ID NO:1).

FIG. 2 is the amino acid sequence of swine GHSR encoded by the DNA of FIG. 1 (SEQ ID NO:2).

FIG. 3 is the entire open reading frame of the type I clone of FIG. 1 (SEQ ID NO:3).

FIG. 4 is the DNA of Swine GHSR (type II) contained in Clone 13751 (SEQ ID NO:4).

FIG. 5 is the amino acid sequence of swine GHSR (type II) encoded by the DNA of FIG. 4 (SEQ ID NO:5).

FIG. 6 is the DNA for human GHSR (Type I) contained in Clone 1146 (SEQ ID NO:6).

FIG. 7 is the amino acid sequence of human GHSR (type 1) encoded by the DNA of FIG. 6 (SEQ ID NO:7).

FIG. 8 is the entire open reading frame of Type I GHSR, encoded by the DNA sequence of FIG. 6 (SEQ ID NO:8).

FIGS. 9A and 9B are the DNA for human GHSR (type II) contained in Clone 1141 (SEQ ID NO:9).

FIG. 10 is the amino acid sequence of human GHSR (Type II) encoded by Clone 1141 (SEQ ID NO:10).

FIG. 11 is the DNA for human GHSR (Type I) contained in Clone 1143 (SEQ ID NO:11).

FIG. 12 is the amino acid sequence of human GHSR (Type I) encoded by Clone 1432 (SEQ ID NO:12).

FIGS. 13A and 13B compare to ORF of swine Type I (SEQ ID NO:3; lacking the MET initiator of the full length GHSR and lacking 12 additional amino acids) to the homologous domain of swine Type II (SEQ ID NO:5) receptors.

FIGS. 14A and 14B compare the homologous domain of human Type I (SEQ ID NO:8) and Type II (SEQ ID NO:10) receptors (the amino terminal sequence lacks the MET initiator and four additional amino acids).

FIG. 15 compares the ORFs of swine Type I (SEQ ID NO:3) and human Type I (SEQ ID NO:8) receptors (the amino terminal sequence lacks the MET initiator and 12 additional amino acids).

FIGS. 16A and 16B compare full length swine Type II (SEQ ID NO:5) and human Type II (SEQ ID NO:10) receptors.

FIG. 22 is the amino acid sequence of the full length human GHSR (type I) encoded by clone 11304 (SEQ ID NO:13).

FIGS. 23A–D are the rat GHSR DNA sequence from the Met Initiation codon to the Stop codon (SEQ ID NO:14). This sequence includes an intron.

FIGS. 24A and 24B are the open reading frame only of the rat GHSR of FIG. 23 (SEQ ID NO:15).

FIG. 25 is the deduced amino acid sequence of the ORF of FIG. 24 (SEQ ID NO:16).

Figure 17:
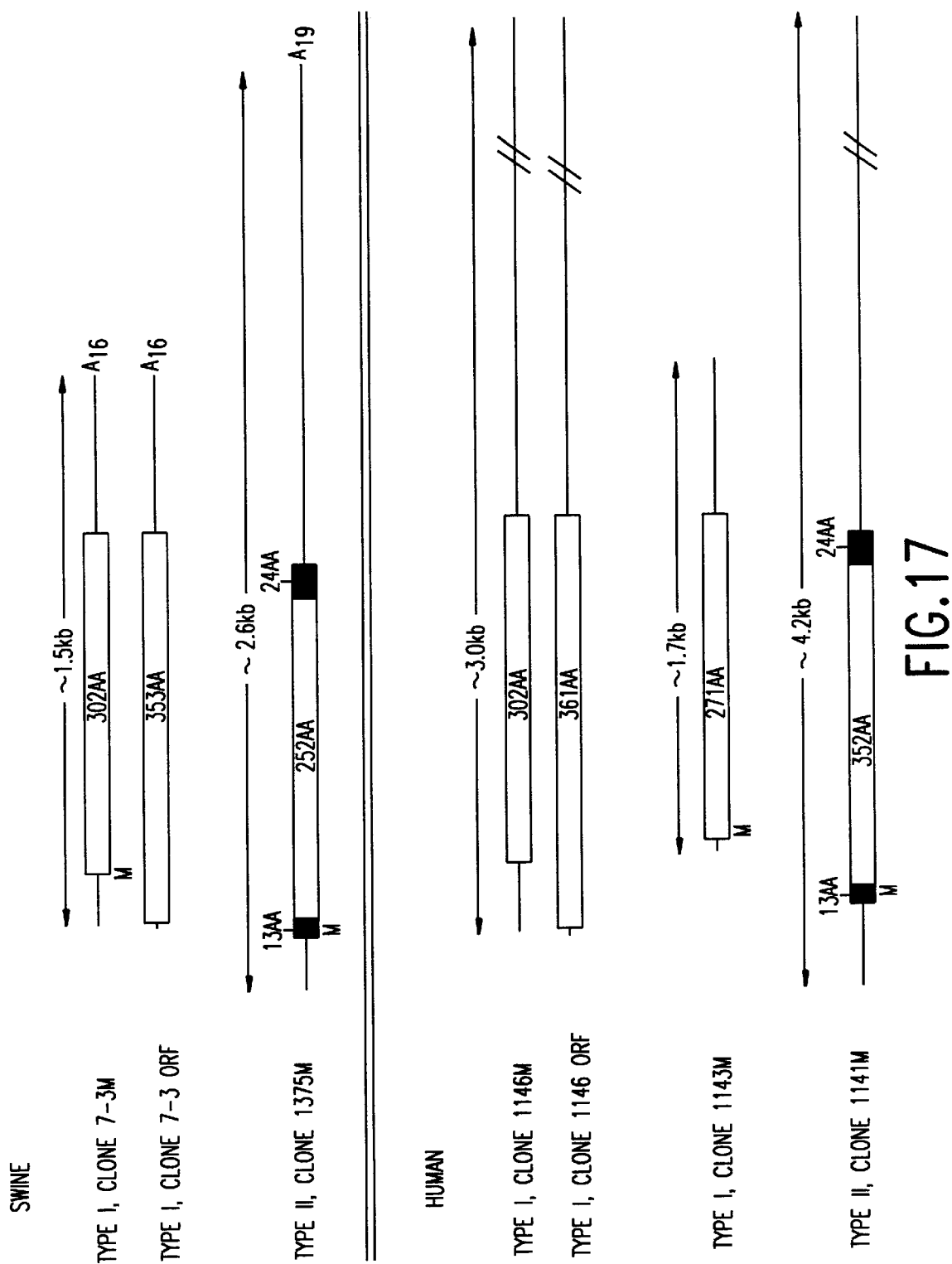
FIG. 17 is a schematic diagram depicting the physical map of swine and human growth hormone secretagogue receptor cDNA clones.

As used throughout the specification and claims, the following definitions shall apply:

Growth Hormone Secretagogue—any compound or agent that directly or indirectly stimulates or increases the release of growth hormone in an animal.

Ligands—any molecule which binds to GHSR of this invention. These ligands can have either agonist, partial agonist, partial antagonist or antagonist activity.

Free from receptor-associated proteins—the receptor protein is not in a mixture or solution with other membrane receptor proteins.

Free from associated nucleic acids—the nucleic acid is not covalently linked to DNA which it is naturally covalently linked in the organism's chromosome.

Isolated receptor—the protein is not in a mixture or solution with any other proteins.

Isolated nucleic acid—the nucleic acid is not in a mixture or solution with any other nucleic acid.

Functional equivalent—a receptor which does not have the exact same amino acid sequence of a naturally occurring growth hormone secretagogue receptor, due to alternative splicing, deletions, mutations, or additions, but retains at least 1%, preferably 10%, and more preferably 25% of the biological activity of the naturally occurring receptor. Such derivatives will have a significant homology with a natural GHSR and can be detected by reduced stringency hybridization with a DNA sequence obtained from A GHSR. The nucleic acid encoding a functional equivalent has at least about 50% homology at the nucleotide level to a naturally occurring receptor nucleic acid.

Purified receptor—the receptor is at least about 95% pure.

Purified nucleic acid—the nucleic acid is at least about 95% pure.

Compound A—(N-[1(R)-[(1,2-dihydro-1-methanesulfonylspiro[3H-indole-3,4'-piperidin]-1'-yl)carbonyl]-2-(phenyl-methyloxy)ethyl]-2-amino-2-methyl propanamide, described in Patchett, 1995 Proc. Natl. Acad. Sci. 92:7001–7005.

Compound B—3-amino-3-methyl-N-(2,3,4,5-tetrahydro-2-oxo-1-{[2'-1H-tetrazol-5-yl)(1,1'-biphenyl)-4-yl]methyl}-1H-benzazepin-3(R)yl-butanamide, described in Patchett, 1995 Proc. Natl. Acad. Sci. 92:7001–7005.

Compound C—3-amino-3-methyl-N-(2,3,4,5-tetrahydro-2-oxo-1-{[2'-1H-tetrazol-5-yl)(1,1'-biphenyl)-4-yl]methyl}1H-benzazepin-3(S)yl-butanamide, described in U.S. Pat. No. 5,206,235.

Standard or high stringency post hybridizational washing conditions—6×SSC at 55° C.

Moderate post hybridizational washing conditions—6× SSC at 45° C.

Relaxed post hybridizational washing conditions—6× SSC at 30° C.

The proteins of this invention were found to have structural features which are typical of the 7-transmembrane domain (TM) containing G-protein linked receptor superfamily (GPC-R's or 7-TM receptors). Thus growth hormone secretagogue family of receptors make up new members of the GPC-R family of receptors. The intact GHSRs of this invention were found to have the general features of GPC-R's, including seven transmembrane regions, three intra- and extracellular loops, and the GPC-R protein signature sequence. The TM domains and GPC-R protein signature sequence are noted in the protein sequences of the Type I GHS receptor in FIGS. 3 and 8 (SEQ ID NOS:3 and 8 respectively. Not all regions are required for functioning, and therefore this invention also comprises functional receptors which lack one or more non-essential domains.

The GHSRs of this invention share some sequence homology with previously cloned GPC-receptors including the rat and human neurotensin receptor (approximately 32% identity) and the rat and human TRH receptor (approximately 30% identity).

The GHSRs of this invention were isolated and characterized using expression cloning techniques in Xenopus oocytes. The cloning was made difficult by three factors. First, prior to this invention, there was very little information available about the biochemical characteristics and intracellular signaling/effector pathways of the proteins. Thus, cloning approaches which depended on the use of protein sequence information for the design of degenerate oligonucleotides to screen cDNA libraries or utilize PCR could not be effectively utilized. In accordance with this invention, therefore, receptor bioactivity needed to be determined.

Secondly, the growth hormone secretagogue receptor does not occur in abundance—it is present on the cell membrane in about 10 fold less concentration than most other membrane receptors. In order to successfully clone the receptors in accordance with this invention, exhaustive precautions had be taken to ensure that the GHSR was represented in a cDNA library to be screened. This required isolation of intact, undegraded and pure poly $(A)^+$ mRNA, and optimization of cDNA synthesis to maximize the production of full-length molecules. In addition, a library of larger size than normal needed to be screened (approximately 0.5 to $1 \times 10^7$ clones) to increase the probability that a functional cDNA clone may be obtained.

Thirdly, no permanent cell line which expresses this receptor is known. Therefore, primary pituitary tissue had to be used as a source for mRNA or protein. This posed an additional obstacle because most primary tissues express lower amounts of a given receptor than an immortalized cell line that may be maintained in tissue culture or some tumor materials. Further, the surgical removal of a pig pituitary and extraction of biologically-active intact mRNA for the construction of a cDNA expression library is considerably more difficult than the extraction of mRNA from a tissue culture cell line. Along with the need to obtain fresh tissue continuously, there are problems associated with its intrinsic inter-animal and inter-preparation variability. The development of cell lines expressing a receptor of this invention is therefore a significant aspect of this invention.

Yet another aspect of this invention is the development of an extremely sensitive, robust, reliable and high-throughput screening assay which could be used to identify portions of a cDNA library containing the receptor. This assay is described and claimed in co-pending patent applications Serial No. 60/008,584, filed Dec. 13, 1995, and filed herewith.

Briefly, the ability to identify cDNAs which encode growth hormone secretagogue receptors depended upon two discoveries made in accordance with this invention: 1) that growth hormone secretagogue receptor-ligand binding events are transduced through G proteins; and 2) that a particular G protein subunit, $G_{\alpha 11}$, must be present in the cells in order to detect receptor activity. Only when these two discoveries were made could an assay be devised to detect the presence of GHSR-encoding DNA sequences.

When the GHSR is bound by ligand (a growth hormone secretagogue), the G-proteins present in the cell activate phosphatidylinositol-specific phospholipase C (PI-PLC), an enzyme which releases intracellular signaling molecules (diacylglycerol and inositol triphosphate), which in turn start a cascade of biochemical events that promote calcium mobilization. This can be used as the basis of an assay. A detector molecule which can respond to changes in calcium concentrations, such as aequorin, a jellyfish photoprotein, is introduced into a cell along with a complex pool of up to 10,000 individual RNAs from a cDNA expression library, at least one of which may encode a GHSR. The cell is then exposed to a known growth hormone secretagogue, such as Compound A or Compound B. If one or more RNAs encodes a GHSR, then the secretagogue ligand will bind the receptor, G-protein will be activated, the calcium level will fluctuate, and the aequorin will produce measurable bioluminescence. Once a positive result is found, the procedure can be repeated with a sub-division of the RNA pool (for example, approximately 1,000, then approximately 500, then approximately 50, and then pure clones) until a single clone is identified from which RNA can be generated which encodes a GHSR.

Using this general protocol in Xenopus oocytes with a swine cDNA expression library, Clone 7-3 was identified as containing nucleic acid encoding a swine GHSR. The insert of the cDNA clone is approximately 1.5 kb in size, and downstream from the presumed initiator methionine (MET), contains an open reading frame (ORF) encoding 302 amino acids ($M_r$=34,516). The DNA and deduced amino acid sequence are given in FIGS. 1 and 2 (SEQ ID NOS:1 and 2, respectively). When hydropathy analysis (e.g. Kyte-Doolittle; Eisenberg, Schwartz, Komaron and Wall) is performed on the protein sequence of clone 7-3, only 6 predicted transmembrane domains are present downstream of the presumed MET initiator. Translation of the longest ORF encoded in clone 7-3 encodes a protein of 353 amino acids ($M_r$=39,787); however an apparent MET initiator cannot be identified for this longer reading frame (FIG. 3). This longer reading frame is significant since 7 transmembrane segments are encoded in the 353 amino acids protein in which a MET translation initiation codon located upstream of TM1 is absent. In addition, this longer protein also shares homology with known G-protein coupled receptors in its predicted TM1 domain (FIG. 3 and next sections). Thus, clone 7-3 while truncated at its amino terminus, is fully functional, demonstrating that clone 7-3 is but one embodiment of a functional equivalent of a native GHSR.

The resultant cDNA clone (or shorter portions of, for instance only 15 nucleotides long) may be used to probe libraries under hybridization conditions to find other receptors which are similar enough so that the nucleic acids can hybridize, and is particularly useful for screening libraries from other species. Using this procedure, additional human, swine, and rat GHSR cDNAs have been cloned and their nucleotide sequences determined. Further, hybridization of a cDNA to genomic DNA demonstrated that the Type I receptor (see below) is encoded by a single gene that is highly conserved. Human, monkey, rat, mouse, dog, cow, chicken and invertebrate DNA all yielded a single hybridizing species at high stringency post-hybridization conditions. Therefore, this invention is not limited to any particular species.

A swine pituitary library, a human pituitary library, and a rat pituitary library were hybridized with a radiolabeled cDNA derived from the open reading frame of the swine GHSR clone 7-3. 21 positive human GHSR cDNA clones were isolated and five swine library pools yielded a strong hybridization signal and contained clones with inserts larger than clone 7-3, as judged by their insert size on Southern blots. A single rat cDNA clone was also isolated.

Nucleotide sequence analysis revealed two types of cDNAs for both the human and swine GHSR cDNAs. The first (Type I) encodes a protein represented by clone 7-3, encoding seven transmembrane domains. The full length open reading frame appears to extend 13 amino acids beyond the largest predicted open reading frame of clone 7-3 (353 amino acids). The second (type II) diverges in its nucleotide sequence from the type I cDNA at its 3'-end, just after the predicted second amino acid of the sixth transmembrane domain (TM-6).

In the type II cDNAs, TM-6 is truncated and fused to a short contiguous reading frame of only 24 amino acids, followed by a translation stop codon. Swine clone 1375 is an example of a, Type II cDNA (FIGS. 4 and 5; SEQ ID.NOs:4 and 5, respectively). These 24 amino acids beyond TM-6 are highly conserved when compared between human and swine cDNAs. The DNA and amino acid sequences of the human GHSR Type I and II are given in FIGS. 6–12; SEQ ID NOs:6–12, respectively. A full length cDNA encoding the human Type I receptor, that is, a molecule encoding 7-TM domains with an initiator MET in a favorable context preceded by an inframe termination codon is isolated, and termed clone 11304. The predicted ORF of clone 11304 for the full length Type I GHSR measures 366 amino acids ($M_r$=41,198; FIG. 22). The full length human Type II cDNA encodes a polypeptide of 289 amino acids ($M_r$=32,156; FIGS. 9A, 9B and 10; SEQ ID NOs: 9 and 10, respectively).

Sequence alignments performed at both the nucleic acid and protein levels show that Type I and II GHSR's are highly related to each other and across species (FIGS. 13–16). The human and swine GHSR sequences are 93% identical and 98% similar at the amino acid level.

The nucleotide sequence encoding the missing amino terminal extension of swine Type I clone 7-3 is derived from the predicted full length human Type I clone and the human and swine Type II cDNAs. The reading frame of the full length clones extended 13 amino acids beyond the amino terminal sequence of clone 7-3 and this sequence was conserved in 12/13 amino acid residues, when compared between human and swine. The amino terminal extension includes a translation initiator methionine in a favorable context according to Kosak's rule, with the reading frame further upstream being interrupted by a stop codon. A schematic physical map of Type I and II swine and human cDNA clones is given in FIG. 17.

The rat clone was also further investigated. Sequence analysis revealed the presence of a non-coding intronic sequence at nt 790 corresponding to a splice-donor site (see FIGS. 23A–D, 24A–B, and 25, respectively). The G/GT splice-donor site occurs two amino acids after the completion of the predicted transmembrane domain 5 (leucine 263), thus dividing the rGHSR into an amino-terminal segment (containing the extracellular domain, TM-1 through TM-5, and the first two intra- and extra-cellular loops) and a carboxy-terminal segment (containing TM-6, TM-7, the third intra- and extra-cellular loops, and the intra-cellular domain). The point of insertion and flanking DNA sequence are highly conserved, and also present in both human and swine Type I and II cDNAs.

Comparison of the complete open reading frame encoding the rat GHSR protein to human and swine homologs reveals a high degree of sequence identity (rat vs. human, 95.1% ; rat vs. swine 93.4%.

The human GHSR can be assigned by fluorescent in situ hybridization analysis [FISH; as described in *Cytogenet,*

*Cell Genet* 69: 196 (1995)] to the cytogenetic band 3Q26.2. The mouse gene is located on 3A3.

Human and swine Type I cRNAs expressed in oocytes were functional and responded to Compound A concentrations ranging from 1 mM to as low as 0.1 nM in the aequorin bioluminescence assay. Human or swine Type II-derived cRNAs that are truncated in TM-6 failed to give a response when injected into oocytes and these represent a receptor subtype which may bind the GHS, but cannot effectively activate the intracellular signal transduction pathway. In addition the type II receptor may interact with other proteins and thus reconstitute a functional GHSR. Proteins such as these which may have ligand-binding activity, but are not active in signal transduction are particularly useful for ligand-binding assays. In these cases, one may also overexpress a mutant protein on the cell membrane and test the binding abilities of putative labeled ligands. By using a non-signaling mutant which is constitutively in a high affinity state, binding can be measured, but no adverse metabolic consequences would result. Thus non-signaling mutants are an important aspect of this invention.

Figures 18, 19:
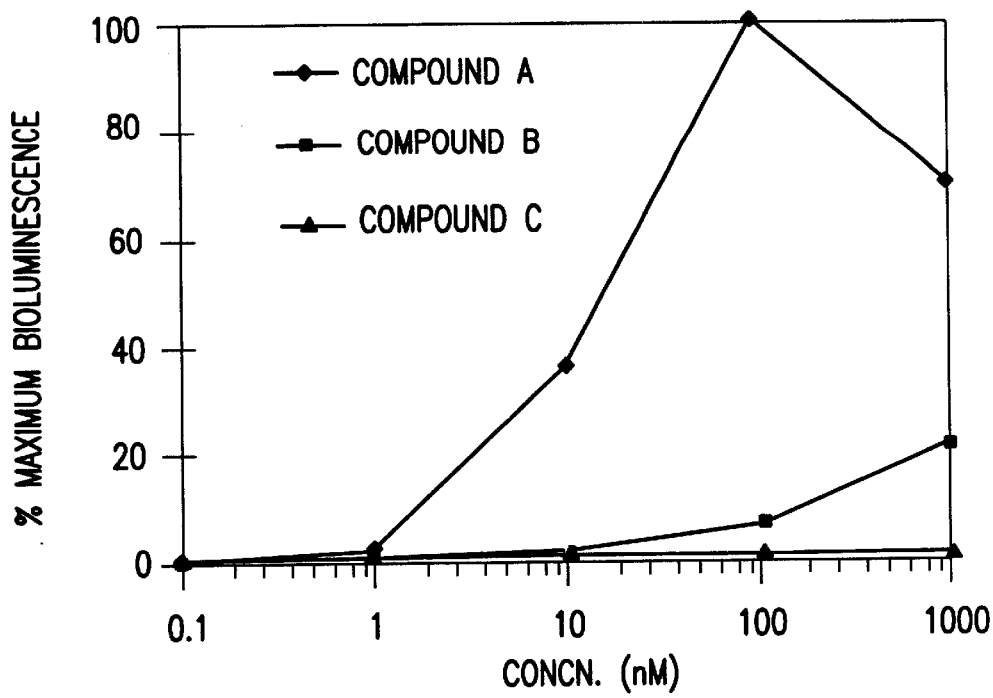
FIG. 18 is a graph demonstrating the pharmacology of the expressed swine and human growth hormone secretagogue receptors in Xenopus oocytes using the aequorin bioluminescence assay.
FIG. 19 is a table demonstrating the pharmacology of the expressed swine and human growth hormone secretagogue receptors in Xenopus oocytes using the aequorin bioluminescence assay and various secretagogues.
Figures 20, 21:
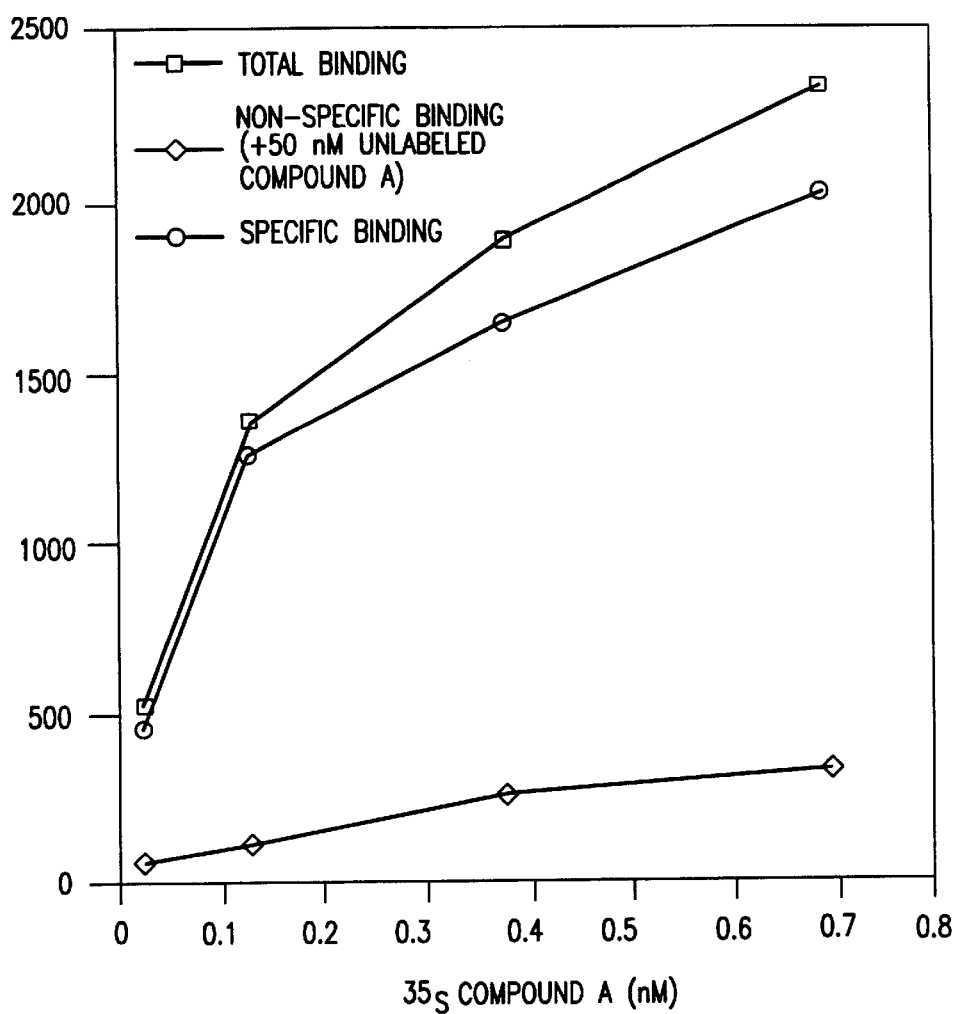
FIG. 20 is a graph representing the pharmacology of the pure expressed swine growth hormone secretagogue receptor in COS-7 cells using the $^{35}$S-labeled Compound A binding assay.
FIG. 21 is a table representing the competition analysis with the pure expressed swine growth hormone secretagogue receptor in COS-7 cells using the $^{35}$S-labeled Compound A binding assay and various secretagogues and other G-protein coupled-receptors (GPC-Receptors) ligands in a competition assay.
Figure 26:
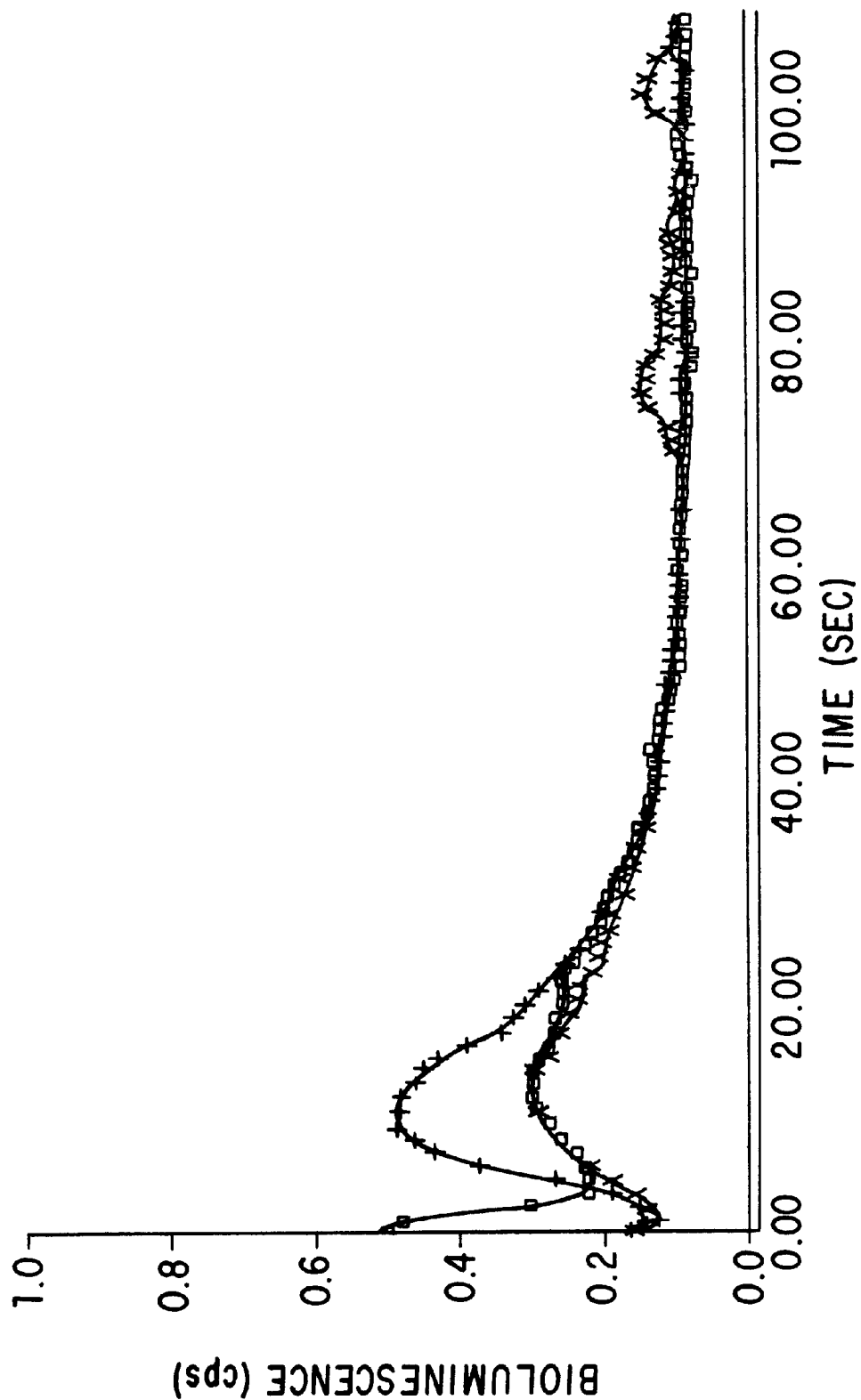
FIG. 26 shows the expression of functional rat GHSR in transfected HEK-293 cells.

The pharmacological characterization of human, Type I swine, Type I and rat receptors in the aequorin bioluminescence assay in oocytes is summarized in FIGS. 18, 19, and 26. Peptidyl and non-peptidyl bioactive GHS's were active in a similar rank order of potency as observed for the native pituitary receptor. Independent confirmatory evidence that the Type I GHSR (shown for swine clone 7-3) encodes a fully-functional GHSR is given by the finding that when clone 7-3 is expressed transiently in mammalian COS-7 cells, high affinity ($K_D \sim 0.2$ nM), saturable ($B_{max} \sim 80$ fmol/mg protein) and specific binding (>90% displaced by 50 nM unlabeled Compound A) is observed for $^{35}$S-Compound A (FIGS. 20 and 21).

The GHSR receptors of this invention may be identified by hybridization of a GHSR cDNA to genomic DNA, under relaxed or moderate post hybridizational washing conditions. This analysis yields a discreet number of hybridizing bands. A suitable human genomic library which can be used in this procedure is PAC (as described in *Nature Genetics* 6:84 (1994)) and a suitable mouse genomic library is BAC (as described in *Proc Natl Acad Sci USA* 89: 8794 (1992).

Due to the high degree of homology to GHSRs, the GHSRs of this invention are believed to function similarly to GHSRs and have similar biological activity. They are useful in understanding the biological and physiological pathways involved in an organisms growth. They may be also used to scan for growth hormone secretagogue agonists and antagonists; as in particular to test the specificity of identified ligands.

Heterotrimeric G proteins, consisting of a, b and g subunits, serve to relay information from cell surface receptors to intracellular effectors, such as phospholipase C and adenylate cyclase. The G-protein alpha subunit is an essential component of the intracellular signal transduction pathway activated by receptor-ligand interaction. In the process of ligand-induced GPCR activation, the Ga subunit of a trimeric Gabg exchanges its bound GDP for GTP and dissociate from the bg heterodimer. The dissociated subunit serves as the active signal transducer, often in concert with the bg complex, thus starting the activation of the intracellular signal transduction pathway. By definition, cell surface receptors which couple intracellularly through G protein interactions are termed GPC-R's. This interaction has mainly been characterized with respect to the type of G-alpha ($G_a$) subunit which is primarily involved in the signal transduction process. $G_a$ subunits are classified into sub-families based on sequence identity and the main type of effectors to which they are coupled have been characterized: $G_s$, activate adenylate cyclase; $G_{i/o/t}$, inhibit adenylate cyclase; $G_{q/11}$, activate PI-PLC; and $G_{12/13}$, effector unknown.

Expression of several receptors in heterologous cells has been shown to be increased by the co-expression of certain $G_a$ subunits. This observation formed the basis for the rationale to the use of $G_a$ subunits of several sub-families in conjunction with a source of GHSR (swine poly[A$^+$] mRNA) to test if a GHS-induced functional response could be measured in the Xenopus oocyte system. GHS-induced responses were detected and were found to be strictly dependent on $G_{a11}$ co-expression in this system, an unprecedented finding outlining the specificity of the interaction. Thus another aspect of this invention is a method of detecting a GHS response comprising co-expressing a $G_{a11}$ protein subunit in a cell also expressing a GHSR, exposing the cell to a GHS, and detecting the response.

Ligands detected using assays described herein may be used in the treatment of conditions which occur when there is a shortage of growth hormone, such as observed in growth hormone deficient children, elderly patients with musculoskeletal impairment and recovering from hip fracture, and osteoporosis.

The GHSR and fragments are immunogenic. Thus, another aspect of this invention is antibodies and antibody fragments which can bind to GHSR or a GHSR fragment. These antibodies may be monoclonal antibodies and produced using either hybridoma technology or recombinant methods. They may be used as part of assay systems or to deduce the function of a GHSR present on a cell membrane.

A further aspect of this invention are antisense oligonucleotides nucleotides which can bind to GHSR nucleotides and modulate receptor function or expression.

A further aspect of this invention is a method of increasing the amount of GHSRs on a cell membrane comprising, introducing into the cell a nucleic acid encoding a GHSR, and allowing expression of the GHSR.

A GHS receptor, preferably imobilized on a solid support, may be used diagnostically for the determination of the concentration of growth hormone secretagogues, or metabolites thereof, in physiological fluids, e.g., body fluids, including serum, and tissue extracts, as for example in patients who are undergoing therapy with a growth hormone secretagogue.

The administration of a GHS receptor to a patient may also be employed for purposes of: amplifying the net effect of a growth hormone secretagogue by providing increased downstream signal following administration of the growth hormone secretagogue thereby diminishing the required dosage of growth hormone secretagogue; or diminishing the effect of an overdosage of a growth hormone secretagogue during therapy.

The following, non-limiting Examples are presented to better illustrate the invention.

EXAMPLE 1

Oocyte Preparation and Selection

*Xenopus laevis* oocytes were isolated and injected using standard methods previously described by Arena, et al., 1991, *Mol. Pharmacol.* 40, 368–374, which is hereby incorporated by reference. Adult female *Xenopus laevis* frogs (purchased from Xenopus One, Ann Arbor, Mich.) were anesthetized with 0.17% tricaine methanesulfonate and the ovaries were surgically removed and placed in a 60 mm culture dish (Falcon) containing OR-2 medium without calcium (82.5 mM NaCl, 2 mM KCl, 2.5 mM sodium pyruvate, 1 mM $MgCl_2$, 100 m/ml penicillin, 1 mg/ml streptomycin, 5 mM HEPES, pH=7.5; ND-96 from Specialty Media, N.J.). Ovarian lobes were broken open, rinsed several times, and oocytes were released from their sacs by collagenase A digestion (Boehringer-Mannheim; 0.2% for 2–3 hours at 18° C.) in calcium-free OR-2. When approximately 50% of the follicular layers were removed, Stage V and VI oocytes were selected and placed in ND-86 with calcium (86 mM NaCl, 2 mM KCl, 1 mM $MgCl_2$, 1.8 mM $CaCl_2$, 2.5 mM sodium pyruvate, 0.5 mM theopylline, 0.1 mM gentamycin, 5 mM HEPES [pH=7.5]). For each round of injection, typically 3–5 frogs were pre-tested for their ability to express a control G-protein linked receptor (human gonadotropin-releasing hormone receptor) and show a robust phospholipase C intracellular signaling pathway (incubation with 1% chicken serum which promotes calcium mobilization by activation of phospholipase C). Based on these results, 1–2 frogs were chosen for library pool injection (50 nl of cRNA at a concentration of 25 ng (complex pools) to 0.5 ng (pure clone) per oocyte usually 24 to 48 hours following oocyte isolation.

EXAMPLE 2
mRNA Isolation

Total RNA from swine (50–80 kg, Yorkshire strain) pituitaries (snap-frozen in liquid nitrogen within 1–2 minutes of animal sacrifice) was prepared by a modified phenol:guanidinium thiocyanate procedure (Chomczynski, et al., 1987 *Anal. Biochem.* 162:156–159, using the TRI-Reagent LS as per the manufacturer's instructions (Molecular Research Center, Cincinnati, Ohio). Typically, 5 mg of total RNA was obtained from 3.5 g wet weight of pituitary tissue. Poly $(A)^+$ RNA was isolated from total RNA by column chromatography (two passes) on oligo (dT) cellulose (Pharmacia, Piscataway, N.J.). The yield of poly $(A)^+$ mRNA from total RNA was usually 0.5%. RNA from other tissues was isolated similarly.

EXAMPLE 3
cDNA Library Construction

First-strand cDNA was synthesized from poly $(A)^+$ mRNA using M-MLV RNAse (−) reverse transcriptase (Superscript, GIBCO-BRL, Gaithersberg, Md.) as per the manufacturer's instructions with an oligo (dT)/Not I primer-adapter. Following second-strand cDNA synthesis, double-stranded cDNA was subjected to the following steps: 1) ligation to EcoR I adapters, 2) Not I digestion, and 3) enrichment for large cDNAs and removal of excess adapters by gel filtration chromatography on a Sephacryl S-500 column (Pharmacia). Fractions corresponding to high molecular weight cDNA were ligated to EcoR I/Not I digested pSV-7, a eucaryotic expression vector capable of expressing cloned cDNA in mammalian cells by transfection (driven by SV-40 promoter) and in oocytes using in vitro transcripts (initiated from the T7 RNA polymerase promoter). pSV-7 was constructed by replacing the multiple cloning site in pSG-5 (Stratagene, La Jolla, Calif.; Green, S. et al., 1988 *Nucleic Acids Res.* 16:369), with an expanded multiple cloning site. Ligated vector:cDNA was transformed into *E.coli* strain DH10B (GIBCO-BRL) by electroporation with a transformation efficiency of $1 \times 10^6$ pfu/10 ng double-stranded cDNA. The library contained approximately $3 \times 10^6$ independent clones with greater than 95% having inserts with an average size approximating 1.65 kb (range 0.8–2.8 kb). Unamplified library stocks were frozen in glycerol at −70° C. until needed. Aliquots of the library were amplified once prior to screening by a modification of a solid-state method (Kriegler, M. in *Gene Transfer and Expression: A Laboratory Manual* Stockton Press, NY 1990). Library stocks were titered on LB plates and then the equivalent of 500–1000 colonies was added to 13 ml of 2×YT media containing 0.3% agarose and 100 mg/ml carbenicillin in a 14 ml round-bottom polypropylene tube (Falcon). The bacterial suspension was chilled in a wet ice bath for 1 hour to solidify the suspension, and then grown upright at 37° C. for 24 hrs. The resultant bacterial colonies were harvested by centrifugation at 2000×g at RT for 10 min, resuspended in 3 ml 2×YT/carbenicillin. Aliquots were taken for frozen stocks (5%) and plasmid DNA preparation.

EXAMPLE 4
Plasmid DNA Preparation and cRNA Transcription

Plasmid DNA was purified from pellets of solid-state grown bacteria (1000 pools of 500 independent clones each) using the Wizard Miniprep kit according to the manufacturer's instructions (Promega Biotech, Madison, Wis.). The yield of plasmid DNA from a 14 ml solid-state amplification was 5–10 mg. In preparation for cRNA synthesis, 4 mg of DNA was digested with Not I, and the subsequent linearized DNA was made protein and RNase-free by proteinase K treatment (10 mg for 1 hour at 37° C.), followed by two phenol, two chloroform/isoamyl alcohol extractions, and two ethanol precipitations. The DNA was resuspended in approximately 15 ml of RNase-free water and stored at −70° C. until needed. cRNA was synthesized using a kit from Promega Biotech with modifications. Each 50 ml reaction contained: 5 ml of linearized plasmid (approximately 1 mg), 40 mM Tris-HCl (pH=7.5), 6 mM $MgCl_2$, 2 mM spermidine, 10 mM NaCl, 10 mM DTT, 0.05 mg/ml bovine serum albumin, 2 units/ml RNasin, 800 mM each of ATP, CTP and UTP, 200 mM GTP, 800 mM m7G(5')ppp(5')G, 80 units of T7 RNA polymerase, and approximately 20,000 cpm of $^{32}$P-CTP as a trace for quantitation of synthesized RNA by TCA precipitation. The reaction was incubated for 3 hrs. at 30° C.; 20 units of RNase-free DNase was added, and the incubation was allowed to proceed for an additional 15 min. at 37° C. cRNA was purified by two phenol, chloroform/isoamyl alcohol extractions, two ethanol precipitations, and resuspended at a concentration of 500 ng/ml in RNase-free water immediately before use.

EXAMPLE 5
Aequorin Bioluminescence Assay (ABA) and Clone Identification

The ABA requires injection of library pool cRNA (25 ng/egg for pool sizes of 500 to 10,000) with aequorin cRNA (2 ng/egg) supplemented with the G-protein alpha subunit $G_{a11}$ (2 ng/egg). To facilitate stabilization of synthetic transcripts from aequorin and $G_{a11}$ plasmids, the expression vector pCDNA-3 was modified (terned pCDNA-3v2) by insertion (in the Apa I restriction enzyme site of the polylinker) of a cassette to append a poly (A) tract on all cRNA's which initiate from the T7 RNA polymerase promoter. This cassette includes (5' to 3'): a Bgl II site, pA (20) and a Sfi I site which can be used for plasmid linearization. Polymerase chain reaction (PCR) was utilized to generate a DNA fragment corresponding to the open reading frame (ORF) of the aequorin cDNA with an optimized Kosak translational initiation sequence (Inouye, S. et. ul., 1985, *Proc. Natl. Acad. Sci. USA* 82:3154–3158). This DNA was ligated into pCDNA-3v2 linearized with EcoR I and Kpn I in the EcoR I/Kpn I site of pCDNA-3v2. $G_{a11}$ cDNA was excised as a Cla I/Not I fragment from the pCMV-5 vector (Woon, C. et. al., 1989 *J. Biol. Chem.* 264: 5697–93), made blunt with Klenow DNA polymerase and inserted into the EcoR V site of pcDNA-3v2. cRNA was injected into oocytes using the motorized "Nanoject" injector (Drummond Sci. Co., Broomall, Pa.) in a volume of 50 nl. Injection needles were pulled in a single step using a Flaming/Brown micropipette puller, Model P-87 (Sutter Instrument Co) and the tips were broken using 53×magnification such that an acute angle was generated with the outside diameter of the needle being <3 mm. Following injection, oocytes were incubated in ND-96 medium, with gentle orbital shaking at 18° C. in the dark. Oocytes were incubated for 24 to 48 hours (depending on the experiment and the time required for expression of the heterologous RNA) before "charging" the expressed aequorin with the essential chromophore coelenterazine. Oocytes were "charged" with coelenterazine by transferring them into 35 mm dishes containing 3 ml charging medium and incubating for 2–3 hours with gentle orbital shaking in the dark at 18° C. The charging medium contained 10 mM coelenterazine (Molecular Probes, Inc., Eugene, Oreg.) and 30 mM reduced glutathione in OR-2 media (no calcium). Oocytes were then returned to ND-86 medium with calcium medium described above and incubation continued in the dark with orbital shaking until bioluminescence measurements were initiated. Measurement of GHSR expression in oocytes was performed using a Berthold Luminometer LB953 (Wallac Inc., Gaithersburg, Md.) connected to a PC running the Autolumat-PC Control software (Wallac Inc., Gaithersburg, Md.). Oocytes (singly or in pairs) were transferred to plastic tubes (75×12 mm, Sarstedt) containing 2.9 ml Ca$^{++}$-free OR-2 medium. Each cRNA pool was tested using a minimum of 3 tubes containing oocytes. Bioluminescence measurements were triggered by the injection of 0.1 ml of 30 mM MK-677 (1 mM final concentration) and recordings were followed for 2 min. to observe kinetic responses consistent with an IP$_3$-mediated response.

Pool S10-20 was prepared from the unfractionated swine pituitary cDNA library and was composed of 10 pools each of 1000 clones. S10-20 gave a positive signal on two luminometer instruments and the component pools were then individually tested for activity. From the 10 pools of 1000 clones, only pool S271 gave a positive response. This pool was made from two pools of 500 clones designated P541 and P542. Again, only one of the pools, P541, gave a positive bioluminescent signal in the presence of 1 mM Compound A. At this point, the bacterial titer was determined in the glycerol stock of P541 such that dilutions could be plated onto LB agar plates containing 100 mg/ml carbenicillin to yield approximately 50 colonies per plate. A total of 1527 colonies were picked and replicated from 34 plates. The colonies on the original plates were then washed off, plasmids isolated, cRNA synthesized and injected into oocytes. cRNA prepared from 8 of the 34 plates gave positive signals in oocytes. Two plates were selected and the individual colonies from these plates were grown up, plasmid isolated, cRNA prepared and injected into oocytes. A single clonal isolate from each plate (designated as clones 7-3 and 28-18) gave a positive bioluminescence response to 1 mM Compound A. Clone 7-3 was further characterized.

EXAMPLE 6
Receptor Characterization

DNA sequencing was performed on both strands using an automated Applied Biosystems instrument (ABI model 373) and manually by the dideoxy chain termination method using Sequenase II (US Biochemical, Cleveland, Ohio). Database searches (Genbank 88, EMBL 42, Swiss-Prot 31, PIR 40, dEST, Prosite, dbGPCR ), sequence alignments and analysis of the GHSR nucleotide and protein sequences were carried out using the GCG Sequence Analysis Software Package (Madison, Wis.; pileup, peptide structure and motif programs), FASTA and BLAST search programs, and the PC/Gene software suite from Intelligenetics (San Francisco, Calif.; protein analysis programs). Northern blot analysis was conducted using total (20 mg/lane) or poly (A)+ mRNA (5–10 mg/lane) prepared as described above. RNA was fractionated on a 1% agarose gel containing 2.2 M formaldehyde and blotted to a nitrocellulose membrane. Southern blots were hybridized with a PCR generated probe encompassing the majority of the ORF predicted by clone 7-3 (nt 291 to 1132). The probe was radiolabeled by random-priming with [a]$^{32}$P-dCTP to a specific activity of greater than 10$^9$ dpm/mg. Southern blots were pre-hybridized at 42° C. for 4 hrs. in 5×SSC, 5×Denhardt's solution, 250 mg/ml tRNA, 1% glycine, 0.075% SDS, 50 mM NaPO$_4$ (pH 6) and 50% formamide. Hybridizations were carried out at 42° C. for 20 hrs. in 5×SSC, 1×Denhardt's solution, 0.1% SDS, 50 mM NaPO$_4$, and 50% formamide. RNA blots were washed in 2×SSC, 0.2% SDS at 42° C. and at −70° C. RNA size markers were 28S and 18S rRNA and in vitro transcribed RNA markers (Novagen). Nylon membranes containing EcoR I and Hind III digested genomic DNA from several species (Clontech; 10 mg/lane) were hybridized for 24 hrs. at 30° C. in 6×SSPE, 10×Denhardt's, 1% SDS, and 50% formamide. Genomic blots were washed twice with room temperature 6×SSPE, twice with 55° C. 6×SSPE, and twice with 55° C. 4×SSPE. Additional swine GHSR clones from the swine cDNA library (described above) were identified by hybridization to plasmid DNA (in pools of 500 clones each) immobilized to nylon membranes in a slot-blot apparatus (Scheicher and Schuell). Pure clonal isolates were subsequently identified by colony hybridization. Swine GHSR clones that extend further in a 5' direction were identified using 5' RACE procedures (Frohman, M. A., 1993 *Methods. Enzymol.* 218:340–358, which is incorporated by reference) using swine pituitary poly (A)$^+$ mRNA as template.

EXAMPLE 7
Human GHSR

Human pituitary homologues of the swine GHSR were obtained by screening a commercially available cDNA library constructed in the vector lambda ZAP II (Stratagene) as per the manufacturer's instructions. Approximately 1.86× 10$^6$ phages were initially plated and screened using a random-primer labeled portion of swine clone 7-3 (described above) as hybridization probe. Twenty one positive clones were plaque purified. The inserts from these clones were excised from the bacteriophage into the phagemid pBluescript II SK- by co-infection with helper phage as described by the manufacturer (Stratagene). Human clones were characterized as has been described above for the swine clone.

EXAMPLE 8
Assays

Mammalian cells (COS-7) were transfected with GHSR expression plasmids using Lipofectamine (GIBCO-BRL; Hawley-Nelson, P. 1993, *Focus* 15:73). Transfections were performed in 60 mm dishes on 80% confluent cells (approximately 4×10$^5$ cells) with 8 mg of Lipofectamine and 32 mg of GHSR plasmid DNA.

Binding of $^{35}$S-Compound A to swine pituitary membranes and crude membranes prepared from COS-7 cells transfected with GHSR expression plasmids was conducted. Crude cell membranes from COS-7 transfectants were prepared on ice, 48 hrs. post-transfection. Each 60 mm dish was washed twice with 3 ml of PBS, once with 1 ml homogenization buffer (50 mM Tris-HCl [pH 7.4], 5 mM MgCl$_2$, 2.5 mM EDTA, 30 mg/ml bacitracin). 0.5 ml of homogenization buffer was added to each dish, cells were removed by scraping and then homogenized using a Polytron device (Brinkmann, Syosset, N.Y.; 3 bursts of 10 sec. at setting 4). The homogenate was then centrifuged for 20 min. at 11,000×g at 0° C. and the resulting crude membrane pellet (chiefly containing cell membranes and nuclei) was resuspended in homogenization buffer supplemented with 0.06% BSA (0.1 ml/60 mm dish) and kept on ice. Binding reactions were performed at 20° C. for 1 hr. in a total volume of 0.5 ml containing: 0.1 ml of membrane suspension, 10 ml of $^{35}$S-Compound A (0.05 to 1 nM; specific activity approximately 900 Ci/ummol), 10 ml of competing drug and 380–390 ml of homogenization buffer. Bound radioligand was separated by rapid vacuum filtration (Brandel 48-well cell harvester) through GF/C filters pretreated for 1 hr. with 0.5% polyethylenimine. After application of the membrane suspension to the filter, the filters were washed 3 times with 3 ml each of ice cold 50 mM Tris-HCl [pH 7.4], 10 mM MgCl$_2$, 2.5 mM EDTA and 0.015% Triton X-100, and the bound radioactivity on the filers was quantitated by scintillation counting. Specific binding (>90% of total) is defined as the difference between total binding and non-specific binding conducted in the presence of 50 nM unlabeled Compound A.

EXAMPLE 9

Preparation of High Specific Activity Radioligand [$^{35}$S]-Compound A

[$^{35}$S]-Compound A was prepared from an appropriate precursor, N-[1(R)-[(1,2-dihydrospiro[3H-indole-3,4'-piperidin]-1'-yl)-carbonyl]-2-(phenyl-methyloxy)ethyl]-2-amino-t-butoxycarbonyl-2-methylpropan-amide, using methane [$^{35}$S]sulfonyl chloride as described in Dean DC, et al., 1995, In: Allen J, Voges R (eds) *Synthesis and Applications of Isotopically Labelled Compounds*, John Wiley & Sons, New York, pp. 795–801. Purification by semi-preparative HPLC (Zorbax SB-phenyl column, 68% MeOH/water, 0.1% TFA, 5 ml/min) was followed by N-t-BOC cleavage using 15% triflyro-acetic acid in dichloromethane (25° C., 3 hr) to give [methylsulfonyl-$^{35}$S]Compound A in near quantitative yield. HPLC purification (Hamilton PRP-1 4.6×250 mm column, linear gradient of 50–75% methanol-water with 1 mM HCl over 30 min, 1.3 ml/min) provided the ligand in >99% radiochemical purity. The structure was established by HPLC coelution with unlabeled Compound A and by mass spectral analysis. The latter method also indicated a specific activity of ~1000 Ci/mmol.

EXAMPLE 10

DNA Encoding a Rat Growth Hormone Secretagogue Receptor (GHSR) Type Ia

Cross-hybridization under reduced stringency was the strategy utilized to isolate the rat GHSR type Ia. Approximately 10$^6$ phage plaques of a once-amplified rat pituitary cDNA library in lambda gt11 (RL1051b; Clontech, Palo Alto, Calif.) were plated on *E. coli* strain Y1090r$^-$. The plaques were transferred to maximum-strength Nytran (Schleicher & Schuell, Keene, N.H.) denatured, neutralized and screened with a 1.6 kb EcoRI/NotI fragment containing the entire coding and untranslated regions of the swine GHSR, clone 7-3. The membranes were incubated at 30° C. in prehybridization solution (50% formamide, 2×Denhardts, 5×SSPE, 0.1% SDS, 100 mg/ml salmon sperm DNA) for 3 hours followed by overnight incubation in hybridization solution (50% formamide, 2×Denhardts, 5×SSPE, 0.1% SDS, 10% dextran sulfate, 100 mg/ml salmon sperm DNA) with 1×10$^6$ cpm/ml of [$^{32}$P]-labeled probe. The probe was labeled with [$^{32}$P]dCTP using a random priming kit (Gibco BRL, Gaithersburg, N.D.). After hybridization the blots were washed two times each with 2×SSC, 0.1% SDS (at 24° C., then 37° C., and finally 55° C.). A single positive clone was isolated following three rounds of plaque purification. Phage containing the GHSR was eluted from plate plaques with 1×lambda buffer (0.1M NaCl, 0.01M MgSO$_4$.7H$_2$O, 35 mM Tris-HCl, pH 7.5) following overnight growth of approximately 200 pfu/150 mm dish. After a ten minute centrifugation at 10,000×g to remove debris, the phage solution was treated with 1 mg/ml RNAse A and DNAse I for thirty minutes at 24° C., followed by precipitation with 20% PEG (8000)/2M NaCl for two hours on ice, and collection by centrifugation at 10,000×g for twenty minutes. Phage DNA was isolated by incubation in 0.1% SDS, 30 mM EDTA, 50 mg/ml proteinase K for one hour at 68° C., with subsequent phenol (three times) and chloroform (twice) extraction before isopropanol precipitation overnight. The GHSR DNA insert (~6.4 kb) was sub-cloned from lambda gt11 into the plasmid vector Litmus 28 (New England Biolabs, Beverly, Mass.). 2 mg of phage DNA was heated to 65° C. for ten minutes, then digested with 100 units BsiWI (New England Biolab, Bevely, Mass.) at 37° C. overnight. A 6.5 kb fragment was gel purified, electroeluted and phenol/chloroform extracted prior to ligation to BsiWI-digested Litmus 28 vector.

Double-stranded DNA was sequenced on both strands on a ABI 373 automated sequencer using the ABI PRISM dye termination cycle sequencing ready reaction kit (Perkin Elmer; Foster City, Calif.).

Comparison of the complete ORF encoding the rat GHSR type Ia protein sequence to human and swine GHSR homologs reveals a high degree of sequence identity (rat vs. human, 95.1%; rat vs. swine 93.4%).

For sequence comparisons and functional expression studies, a contiguous DNA fragment encoding the complete ORF (devoid of intervening sequence) for the rat GHSR type Ia was generated. The PCR was utilized to synthesize a amino-terminal fragment from Met-1 to Val-260 with EcoRI (5') and HpaI (3') restriction sites appended, while a carboxyl-terminal fragment was generated from Lys-261 to Thr-364 with Dra 1 (5') and Not I (3') restriction sites appended. The ORF construct was assembled into the mammalian expression vector pSV7 via a three-way ligation with EcoRi/Not I-digested pSV7, EcoRI/Hpa I-digested NH$_2$-terminal fragment, and Dra I/Not I-digested C-terminal fragment.

Functional activity of the ORF construct was assessed by transfecting (using lipofectamine; GIBCO/BRL) 5 mg of plasmid DNA into the aequorin expressing reporter cell line (293-AEQ17) cultured in 60 mm dishes. Following approximately 40 hours of expression the aequorin in the cells was charged for 2 hours with coelenterazine, the cells were harvested, washed and pelleted by low speed centrifugation into luminometer tubes. Functional activity was determined by measuring Compound A dependent mobilization of intracellular calcium and concomitant calcium induced aequorin bioluminescence. Shown in FIG. 26 are three replicate samples exhibiting Compound A-induced luminescent responses.

What is claimed is:

1. An isolated swine growth hormone secretagogue receptor which comprises the amino acid sequence of SEQ ID NO: 3.

2. An isolated human growth hormone secretagogue receptor which comprises the amino acid sequence of SEQ ID NO: 7.

3. An isolated rat growth hormone secretagogue receptor which comprises the amino acid sequence of SEQ ID NO: 16.

4. An isolated nucleic acid which encodes swine growth hormone secretagogue receptor which is that of SEQ ID NO: 1.

5. A vector comprising a nucleic acid which encodes a growth hormone secretagogue receptor in accordance with claim 4.

6. A vector according to claim 5 which is selected from the group consisting of: plasmnids, modified, viruses, yeast artificial chromosomes, bacteriophages, cosmids and transposable elements.

7. A host cell comprising a vector according to claim 6.

8. An isolated nucleic acid which encodes human growth hormone secretagogue receptor which is that of SEQ ID NOs: 6, 11 or 13.

9. A vector comprising a nucleic acid which encodes a growth hormone secretagogue receptor in accordance with claim 8.

10. A vector according to claim 9 which is selected from the group consisting of: plasmids, modified viruses, yeast artificial chromosomes, bacteriophages, cosmids and transposable elements.

11. A host cell comprising a vector according to claim 10.

12. An isolated nucleic acid which encodes rat growth hormone secretagogue receptor which is that of SEQ ID NO: 14 or SEQ ID NO: 15.

13. A vector comprising a nucleic acid which encodes a growth hormone secretagogue receptor in accordance with claim 12.

14. A vector according to claim 13 which is selected from the group consisting of: plasmids, modified viruses, yeast artificial chromosomes, bacteriophages, cosmids and transposable elements.

15. A host cell comprising a vector according to claim 14.

16. A growth hormone secretagogue receptor, free from receptor-associated proteins which comprises the amino acid sequence of SEQ ID NO: 3.

17. An isolated human growth hormone secretagogue receptor which comprises the amino acid sequence of SEQ ID NO: 8.

18. An isolated human growth hormone secretagogue receptor which comprises the amino acid sequence of SEQ ID NO: 12.

19. An isolated human growth hormone secretagogue receptor which comprises the amino acid sequence of SEQ ID NO: 13.

20. A growth hormone secretagogue receptor, free from receptor-associated proteins which comprises the amino acid sequence of SEQ ID NO: 7.

21. A growth hormone secretagogue receptor, free from receptor-associated proteins which comprises the amino acid sequence of SEQ ID NO: 8.

22. A growth hormone secretagogue receptor, free from receptor-associated proteins which comprises the amino acid sequence of SEQ ID NO: 12.

23. A growth hormone secretagogue receptor, free from receptor-associated proteins which comprises the amino acid sequence of SEQ ID NO: 13.

24. A growth hormone secretagogue receptor, free from receptor-associated proteins which comprises the amino acid sequence of SEQ ID NO: 16.

* * * * *